(12) United States Patent
Singh et al.

(10) Patent No.: US 9,987,042 B2
(45) Date of Patent: Jun. 5, 2018

(54) GENERAL UTERINE MANIPULATOR AND SYSTEM

(71) Applicants: Jai Singh, Woodvale (AU); Jiwan Steven Singh, Woodvale (AU)

(72) Inventors: Jai Singh, Woodvale (AU); Jiwan Steven Singh, Woodvale (AU)

( * ) Notice: Subject to any disclaimer, the term of this patent is extended or adjusted under 35 U.S.C. 154(b) by 254 days.

(21) Appl. No.: 14/722,025

(22) Filed: May 26, 2015

(65) Prior Publication Data

US 2016/0081717 A1  Mar. 24, 2016

Related U.S. Application Data

(63) Continuation of application No. 14/498,166, filed on Sep. 26, 2014, now Pat. No. 9,101,390, which is a
(Continued)

(51) Int. Cl.
*A61B 17/42* (2006.01)
*A61B 17/46* (2006.01)
(Continued)

(52) U.S. Cl.
CPC .......... *A61B 17/4241* (2013.01); *A61B 17/42* (2013.01); *A61B 90/30* (2016.02);
(Continued)

(58) Field of Classification Search
CPC . A61B 17/4241; A61B 17/34; A61B 17/3415; A61B 17/3421; A61B 17/3423;
(Continued)

(56) References Cited

U.S. PATENT DOCUMENTS 2,191,721 A * 2/1940 Milarch ................. A46B 15/00
132/75.3
2,201,372 A * 5/1940 Miller ..................... F16L 21/08
277/619
(Continued)

FOREIGN PATENT DOCUMENTS

AU         773391          5/2004
AU     2011101651 A4       2/2012
(Continued)

OTHER PUBLICATIONS

SecuFix Uterus Manipulator, 4 pages, www.richard-wolf.com. The "publication date" of this reference is not readily available. Applicant requests that the Examiner review the reference as prior art. Applicant reserves the right to disqualify the reference as prior art if needed.
(Continued)

*Primary Examiner* — Amy R Weisberg
(74) *Attorney, Agent, or Firm* — Knobbe, Martens, Olson & Bear, LLP

(57) ABSTRACT

A medical instrument configured to be inserted into a body cavity comprises a body comprises a first probe at a first end, the first probe comprising a first cylindrical portion with a first outer circumferential surface of a first diameter; a first circumferential edge at a distal end of the first probe; a first distal lip projecting outwardly from the first outer circumferential surface beyond the first circumferential edge and extending for at least a part of a circumference of the first circumferential edge; and a first marker lip projecting outwardly from the first outer circumferential surface and extending for at least a part of a circumference of the first outer circumferential surface; wherein the first distal lip is positioned distal to the first marker lip; and wherein the body
(Continued)

comprises a hollow cavity to enable a second medical instrument to pass therethrough.

45 Claims, 26 Drawing Sheets

Related U.S. Application Data continuation of application No. PCT/US2013/061180, filed on Sep. 23, 2013, which is a continuation-in-part of application No. 13/720,086, filed on Dec. 19, 2012, now abandoned, which is a continuation-in-part of application No. 13/625,255, filed on Sep. 24, 2012, now abandoned, which is a continuation-in-part of application No. PCT/AU2012/000332, filed on Mar. 30, 2012.

(60) Provisional application No. 61/472,705, filed on Apr. 7, 2011.

(51) Int. Cl.
- A61D 1/10 (2006.01)
- A61B 90/30 (2016.01)
- A61B 17/00 (2006.01)
- A61B 10/02 (2006.01)
- A61B 90/00 (2016.01)
- A61B 19/00 (2006.01)

(52) U.S. Cl.
CPC .......... A61B 10/0291 (2013.01); A61B 19/54 (2013.01); A61B 2017/00398 (2013.01); A61B 2017/00464 (2013.01); A61B 2017/00473 (2013.01); A61B 2017/4216 (2013.01); A61B 2090/306 (2016.02); A61B 2090/309 (2016.02); A61B 2090/3962 (2016.02)

(58) Field of Classification Search
CPC ...... A61B 2017/345; A61B 2019/5462; A61B 1/00073; A61B 1/00075; A61B 2017/3458; A61M 25/00; A61M 2025/006; A61M 2025/0293; A61M 39/00; A61M 39/10; A61M 39/02; A61M 5/34; A61M 25/0014; A61M 2039/1027; A61M 2039/1033; A61F 2002/30884; A61F 2220/0016
USPC ................ 606/119, 108, 191; 604/264
See application file for complete search history.

(56) References Cited

U.S. PATENT DOCUMENTS

| | | | | |
|---|---|---|---|---|
| 2,400,251 A * | 5/1946 | Nagel | A61B 17/4241 | 606/119 |
| 2,470,308 A * | 5/1949 | Haddican | F16L 13/007 | 285/132.1 |
| 2,636,598 A * | 4/1953 | Hopgood | A45D 40/06 | 401/30 |
| 2,707,471 A * | 5/1955 | Koff | A61M 29/00 | 600/6 |
| 3,465,529 A * | 9/1969 | Bernd-Heinz | B60R 1/06 | 210/170.01 |
| 3,926,192 A * | 12/1975 | Van Maren | A61B 17/4241 | 604/523 |
| 4,045,027 A * | 8/1977 | Manska | A63B 67/083 | 473/509 |
| 4,117,847 A * | 10/1978 | Clayton | A61F 5/4408 | 604/179 |
| 4,207,872 A * | 6/1980 | Meiri | A61B 1/31 | 254/134.6 |
| 4,382,445 A * | 5/1983 | Sommers | A61M 25/0075 | 604/8 |
| 4,430,076 A * | 2/1984 | Harris | A61M 25/1011 | 600/435 |
| 4,840,613 A * | 6/1989 | Balbierz | A61M 5/158 | 604/163 |
| 4,859,067 A | 8/1989 | Hoppe et al. | | |
| 4,863,133 A | 9/1989 | Bonnell | | |
| 4,863,174 A * | 9/1989 | Cummings | A63B 67/083 | 273/412 |
| 4,998,924 A * | 3/1991 | Ranford | A61M 5/3271 | 604/110 |
| 5,003,146 A * | 3/1991 | Alexander | B23K 9/282 | 219/69.1 |
| 5,052,998 A * | 10/1991 | Zimmon | A61F 2/94 | 604/530 |
| 5,112,346 A | 5/1992 | Hiltebrandt et al. | | |
| 5,138,228 A * | 8/1992 | Thomas | H01J 61/33 | 313/284 |
| 5,156,599 A * | 10/1992 | Ranford | A61M 5/3271 | 128/919 |
| 5,167,614 A * | 12/1992 | Tessmann | A61F 2/92 | 604/8 |
| 5,191,888 A * | 3/1993 | Palmer | A61M 25/0905 | 600/434 |
| 5,205,831 A * | 4/1993 | Ryan | A61M 39/0613 | 604/533 |
| 5,320,613 A * | 6/1994 | Houge | A61M 25/00 | 604/256 |
| 5,338,313 A * | 8/1994 | Mollenauer | A61M 39/0613 | 251/4 |
| 5,395,331 A * | 3/1995 | O'Neill | A61M 25/0023 | 604/103.08 |
| 5,425,739 A * | 6/1995 | Jessen | A61B 17/11 | 606/153 |
| 5,472,419 A * | 12/1995 | Bacich | A61B 17/435 | 600/35 |
| 5,487,377 A | 1/1996 | Smith et al. | | |
| 5,501,690 A | 3/1996 | Measamer et al. | | |
| 5,542,321 A * | 8/1996 | Fuca | B25B 13/02 | 81/124.2 |
| 5,643,285 A * | 7/1997 | Rowden | A61B 17/4241 | 606/119 |
| 5,741,333 A * | 4/1998 | Frid | A61F 2/90 | 623/1.18 |
| RE35,849 E * | 7/1998 | Soehendra | A61F 2/94 | 604/286 |
| 5,782,916 A * | 7/1998 | Pintauro | A61F 2/0022 | 600/30 |
| 5,792,165 A | 8/1998 | Klieman et al. | | |
| 5,800,514 A * | 9/1998 | Nunez | A61F 2/06 | 139/384 R |
| 5,840,077 A * | 11/1998 | Rowden | A61B 17/4241 | 606/119 |
| 5,876,383 A * | 3/1999 | Grooters | A61M 25/0068 | 604/264 |
| 5,931,820 A * | 8/1999 | Morse | A61M 3/0279 | 604/411 |
| 5,947,954 A * | 9/1999 | Bonaldo | A61M 39/22 | 604/248 |
| 5,957,423 A | 9/1999 | Kronner | | |
| 6,004,302 A * | 12/1999 | Brierley | A61F 9/00781 | 604/239 |
| 6,010,520 A | 1/2000 | Pattison | | |
| 6,086,606 A | 7/2000 | Knodel et al. | | |
| 6,096,022 A * | 8/2000 | Laymon | A61M 25/00 | 604/523 |
| 6,124,523 A * | 9/2000 | Banas | A61F 2/07 | 606/191 |
| 6,203,532 B1 * | 3/2001 | Wright | A61M 39/12 | 604/264 |
| 6,254,578 B1 * | 7/2001 | Grooters | A61M 25/0068 | 604/264 |
| 6,371,981 B1 * | 4/2002 | Yang | A61B 17/11 | 623/1.13 |

(56) References Cited

U.S. PATENT DOCUMENTS

| | | | |
|---|---|---|---|
| 6,423,075 B1* | 7/2002 | Singh | A61B 17/4241 128/DIG. 26 |
| 6,516,216 B1* | 2/2003 | Fontenot | A61B 1/00167 600/473 |
| 6,517,570 B1* | 2/2003 | Lau | A61F 2/88 606/195 |
| 6,572,593 B1* | 6/2003 | Daum | A61B 17/34 604/164.13 |
| 6,589,213 B2* | 7/2003 | Reydel | A61M 25/0043 600/585 |
| 6,692,504 B2* | 2/2004 | Kurz | A61B 17/22031 604/106 |
| 6,758,834 B2* | 7/2004 | Grooters | A61M 25/0068 604/264 |
| 6,767,339 B2* | 7/2004 | Reydel | A61M 25/0043 604/175 |
| 6,811,547 B2* | 11/2004 | Wilkinson | A61B 5/15003 604/192 |
| 6,893,428 B2* | 5/2005 | Willemstyn | A61M 39/165 604/163 |
| 7,044,962 B2* | 5/2006 | Elliott | A61F 2/07 623/1.13 |
| 7,195,641 B2* | 3/2007 | Palmaz | A61F 2/2418 623/1.26 |
| 7,338,530 B2* | 3/2008 | Carter | A61F 2/07 623/23.66 |
| 7,811,148 B2* | 10/2010 | Fridrich | C03B 23/049 445/26 |
| 7,811,278 B2* | 10/2010 | Knipple, Jr. | A61M 16/0816 604/533 |
| 7,993,328 B2* | 8/2011 | Whitley | A61M 39/1011 604/537 |
| 8,042,775 B1 | 10/2011 | Gallegos | |
| 8,052,650 B2* | 11/2011 | Young | A61J 15/0069 604/174 |
| 8,287,517 B2* | 10/2012 | Hanlon | A61H 9/0078 604/533 |
| 8,298,213 B2* | 10/2012 | Singh | A61B 17/4241 600/204 |
| 8,495,809 B2 | 7/2013 | Valtchev | |
| 8,567,754 B1* | 10/2013 | Gilstad | F04B 53/1022 137/516.29 |
| 8,568,423 B2* | 10/2013 | Boebel | A61B 17/4241 606/119 |
| 8,574,221 B2* | 11/2013 | Deeds | A61M 39/08 604/523 |
| 8,603,105 B2 | 12/2013 | Sauer | |
| 8,623,070 B2* | 1/2014 | Bales | A61F 2/88 623/1.22 |
| 8,647,325 B2* | 2/2014 | Charlez | A61M 1/3653 604/523 |
| 8,647,326 B2* | 2/2014 | Solomon | A61M 39/162 422/28 |
| 8,647,349 B2* | 2/2014 | Gruber | A61B 17/12045 606/119 |
| 8,663,239 B2* | 3/2014 | Hess | A61B 90/30 606/119 |
| 8,709,362 B2* | 4/2014 | Leventhal | B01L 3/18 422/547 |
| 8,740,916 B2* | 6/2014 | Blair | A61B 17/4241 606/119 |
| 8,770,200 B2* | 7/2014 | Ahluwalia | A61F 6/06 128/830 |
| 8,876,800 B2* | 11/2014 | Behan | A61F 2/0009 604/540 |
| 8,876,886 B2* | 11/2014 | Kaufmann | A61F 2/90 606/108 |
| 9,101,390 B2 | 8/2015 | Singh et al. | |
| 9,451,985 B2 | 9/2016 | Singh et al. | |
| 9,532,837 B2 | 1/2017 | Singh et al. | |
| 2002/0095160 A1* | 7/2002 | Bonutti | A61B 17/3439 606/119 |
| 2003/0100881 A1* | 5/2003 | Hwang | A61B 5/150732 604/403 |
| 2004/0097961 A1 | 5/2004 | Burbank et al. | |
| 2004/0204720 A1* | 10/2004 | Harrington | A61B 17/12109 606/119 |
| 2004/0236285 A1* | 11/2004 | Fisher | A61M 5/3158 604/207 |
| 2005/0085827 A1* | 4/2005 | G. | A61B 17/4241 606/119 |
| 2005/0277948 A1* | 12/2005 | Cedars | A61B 17/42 606/119 |
| 2006/0254115 A1* | 11/2006 | Thomas | F41G 1/38 42/122 |
| 2007/0135819 A1* | 6/2007 | Spiritos | A61B 17/4241 606/119 |
| 2008/0039865 A1* | 2/2008 | Shaher | A61B 17/0206 606/119 |
| 2008/0154244 A1* | 6/2008 | Singh | A61B 17/4241 606/1 |
| 2009/0048609 A1* | 2/2009 | Atiomo | A61B 17/42 606/119 |
| 2009/0062839 A1* | 3/2009 | Kurrus | A61B 17/12022 606/198 |
| 2009/0137970 A1* | 5/2009 | George | A61B 17/4241 604/271 |
| 2009/0138043 A1* | 5/2009 | Kohm | A61B 17/3421 606/246 |
| 2010/0160928 A1 | 6/2010 | Navas | |
| 2010/0268308 A1* | 10/2010 | Rossby | A61M 39/0247 607/116 |
| 2010/0274260 A1* | 10/2010 | D'Arpiany | A61B 17/42 606/119 |
| 2011/0009704 A1* | 1/2011 | Marczyk | A61B 17/3423 600/207 |
| 2011/0282368 A1* | 11/2011 | Swayze | A61B 17/0057 606/159 |
| 2011/0306829 A1* | 12/2011 | Sharp | A61B 17/3421 600/104 |
| 2012/0109124 A1 | 5/2012 | Morozov | |
| 2012/0143209 A1* | 6/2012 | Brecheen | A61B 17/42 606/119 |
| 2012/0143210 A1 | 6/2012 | Brecheen et al. | |
| 2012/0330324 A1* | 12/2012 | Sauer | A61B 17/4241 606/119 |
| 2013/0066328 A1* | 3/2013 | Singh | A61B 17/42 606/119 |
| 2013/0150682 A1* | 6/2013 | Rebuffat | A61B 1/31 600/208 |
| 2013/0197536 A1* | 8/2013 | Singh | A61B 17/4241 606/119 |
| 2014/0052144 A1 | 2/2014 | Singh et al. | |
| 2014/0100595 A1* | 4/2014 | Morgenstern Lopez | A61B 17/1757 606/191 |
| 2014/0135587 A1 | 5/2014 | Hess | |
| 2014/0265319 A1* | 9/2014 | Clark | A61M 39/1011 285/330 |
| 2014/0276916 A1* | 9/2014 | Ahluwalia | A61B 17/4241 606/119 |
| 2014/0303641 A1* | 10/2014 | Boebel | A61B 17/4241 606/119 |
| 2015/0012009 A1* | 1/2015 | Singh | A61B 17/4241 606/119 |
| 2015/0126813 A1* | 5/2015 | Rebuffat | A61B 1/31 600/203 |
| 2015/0133958 A1 | 5/2015 | Singh et al. | |

FOREIGN PATENT DOCUMENTS

| | | |
|---|---|---|
| AU | 2007335226 | 9/2012 |
| CA | 2778976 | 8/2012 |
| CN | 201005764 | 1/2008 |
| DE | 10208508 | 1/2003 |
| EP | 0400458 | 12/1990 |
| JP | 2006-122674 | 10/2005 |
| JP | 2009-273891 | 11/2009 |

(56) References Cited

FOREIGN PATENT DOCUMENTS

| JP | 2011-104399 | 6/2011 |
|---|---|---|
| KR | 10-2001-0052102 A | 6/2001 |
| WO | WO 2008/074054 | 6/2008 |
| WO | WO 2008/136024 | 9/2008 |
| WO | WO 2010/151429 | 12/2010 |
| WO | WO 2011/140604 | 9/2011 |
| WO | WO 2012/135893 | 10/2012 |
| WO | WO 2013/159019 | 10/2013 |
| WO | WO 2013/102235 | 11/2013 |
| WO | WO 2014/047554 | 3/2014 |

OTHER PUBLICATIONS

Cooper Surgical, "Uterine Positioning System™ Facilitates accurate and secure uterine placement," Brochure, revision Dec. 2008, in 5 pages, Trumbull, CT.

Surgitools, Instructions for Use: Singh MultiGuide ARC, Apr. 30, 2013.

International Preliminary Report on Patentability for PCT Application No. PCT/AU2012/000332, dated Feb. 27, 2013.

International Search Report and Written Opinion, International Application No. PCT/AU2012/000332, International Filing Date, Mar. 30, 2012, dated May 17, 2012.

International Search Report and Written Opinion for PCT Application No. PCT/US2013/061180, dated Dec. 17, 2013.

International Search Report and Written Opinion for PCT/US2013/037417, dated Jul. 29, 2013.

International Search Report and Written Opinion for PCT/AU2012/001515, dated Feb. 4, 2013.

Ob.gyn.news, "Kronner non-Pneumatic Scope/Instrument Holder for laparoscopic and other endoscopic surgery," updated Mar. 16, 2013, in 2 pages, product.zone.obgynnews.com.

R. Kronner, Md Facs, "The Kronner Side-Kick: A Perineal Instrument Holder," manual in 13 pages, Kronner Medical, Roseburg, Oregon.

Stryker, "Give Yourself A Hand," Stryker Endoscopy Brochure, in 2 pages, 2006, Stryker, San Jose, CA.

\* cited by examiner

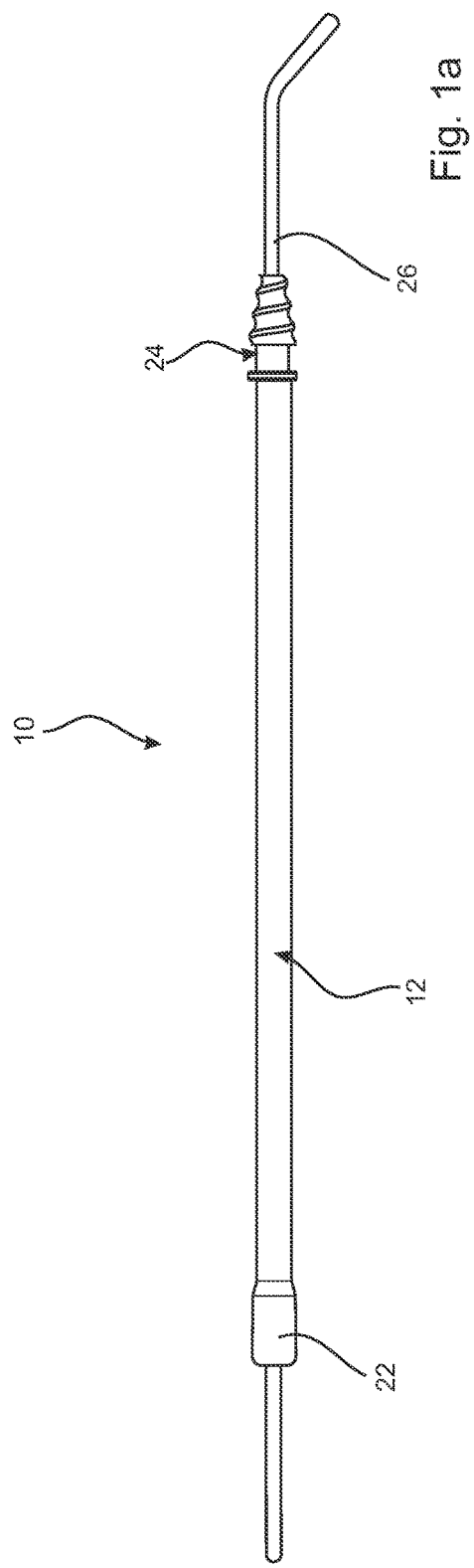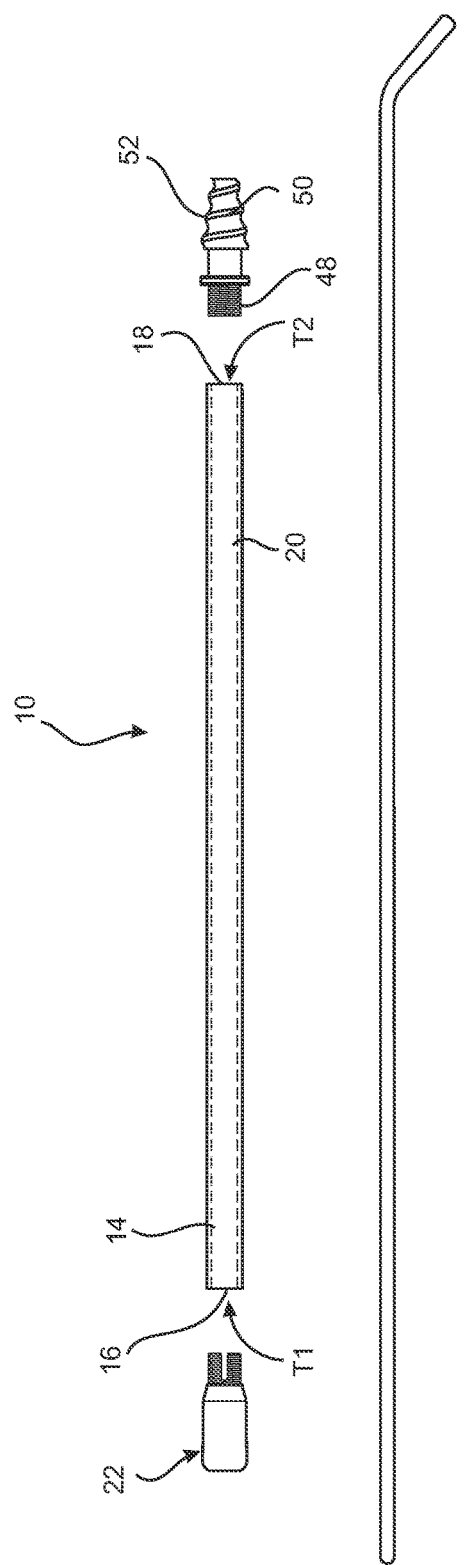

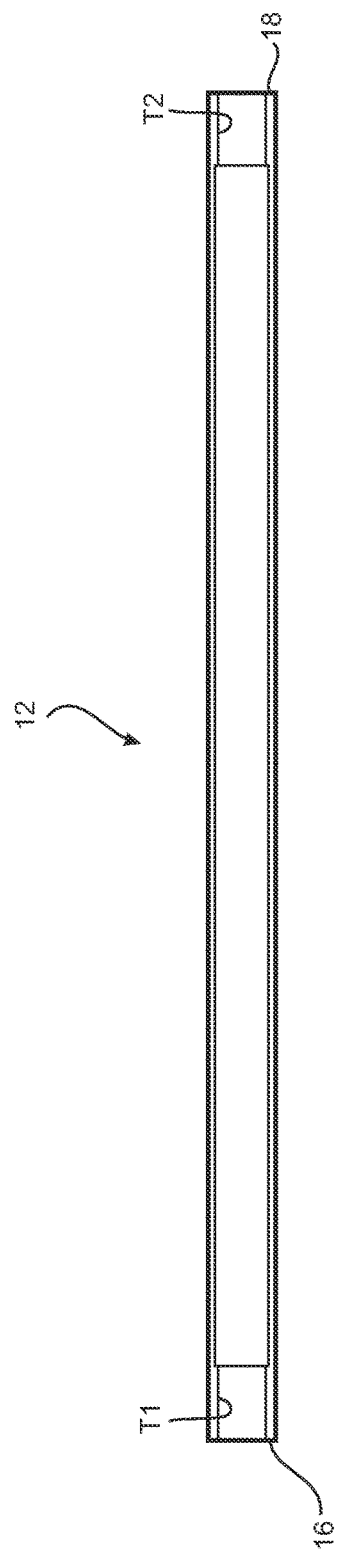

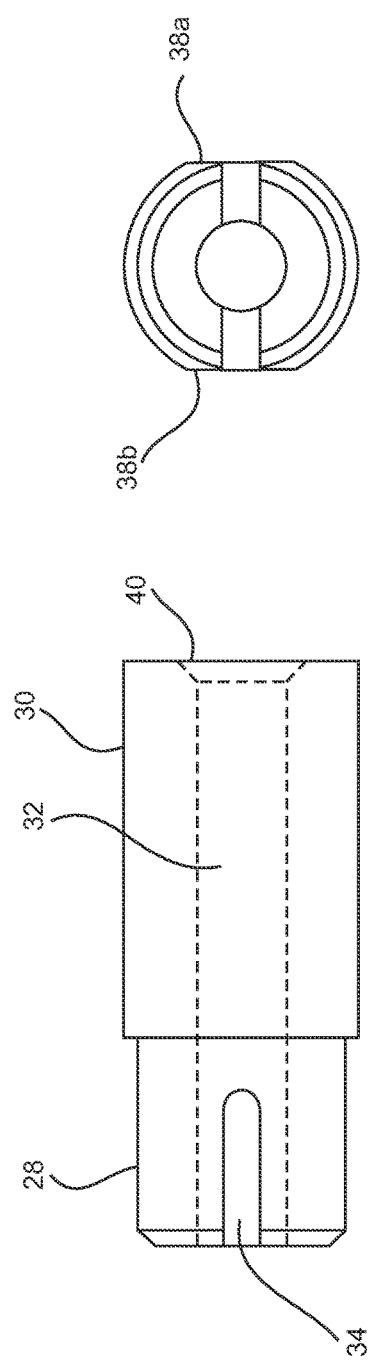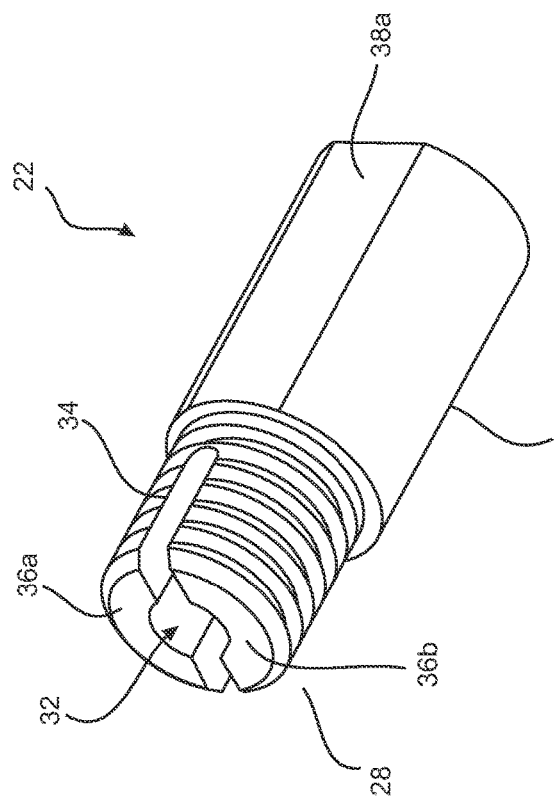

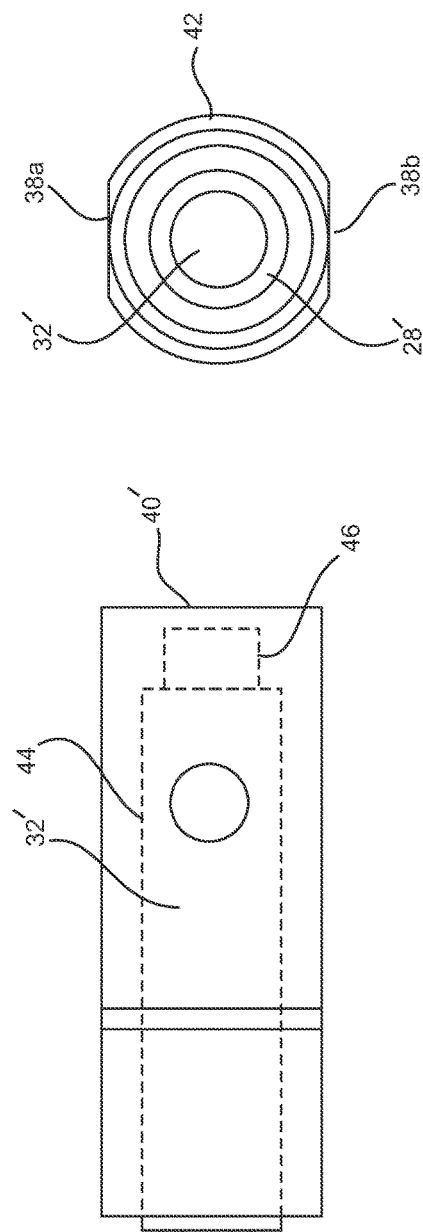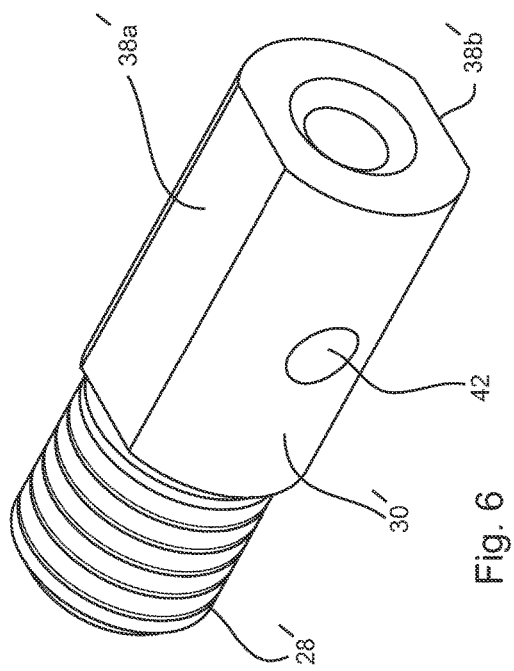

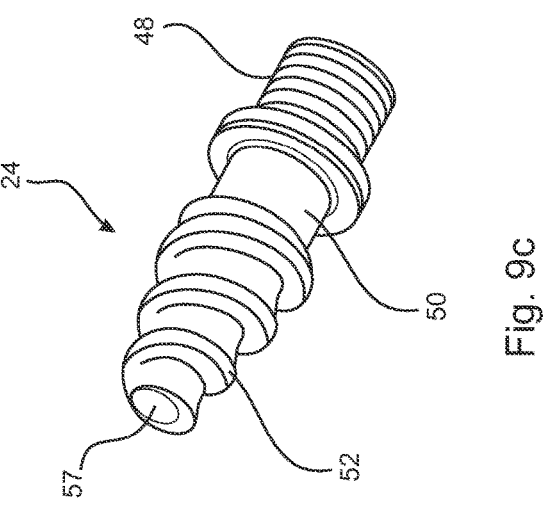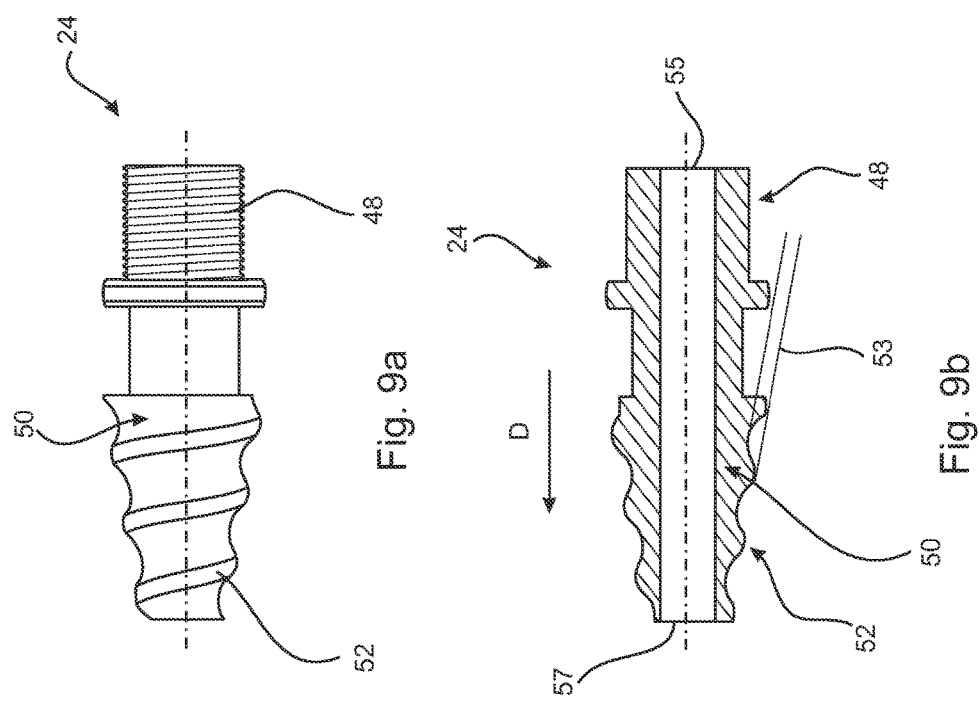

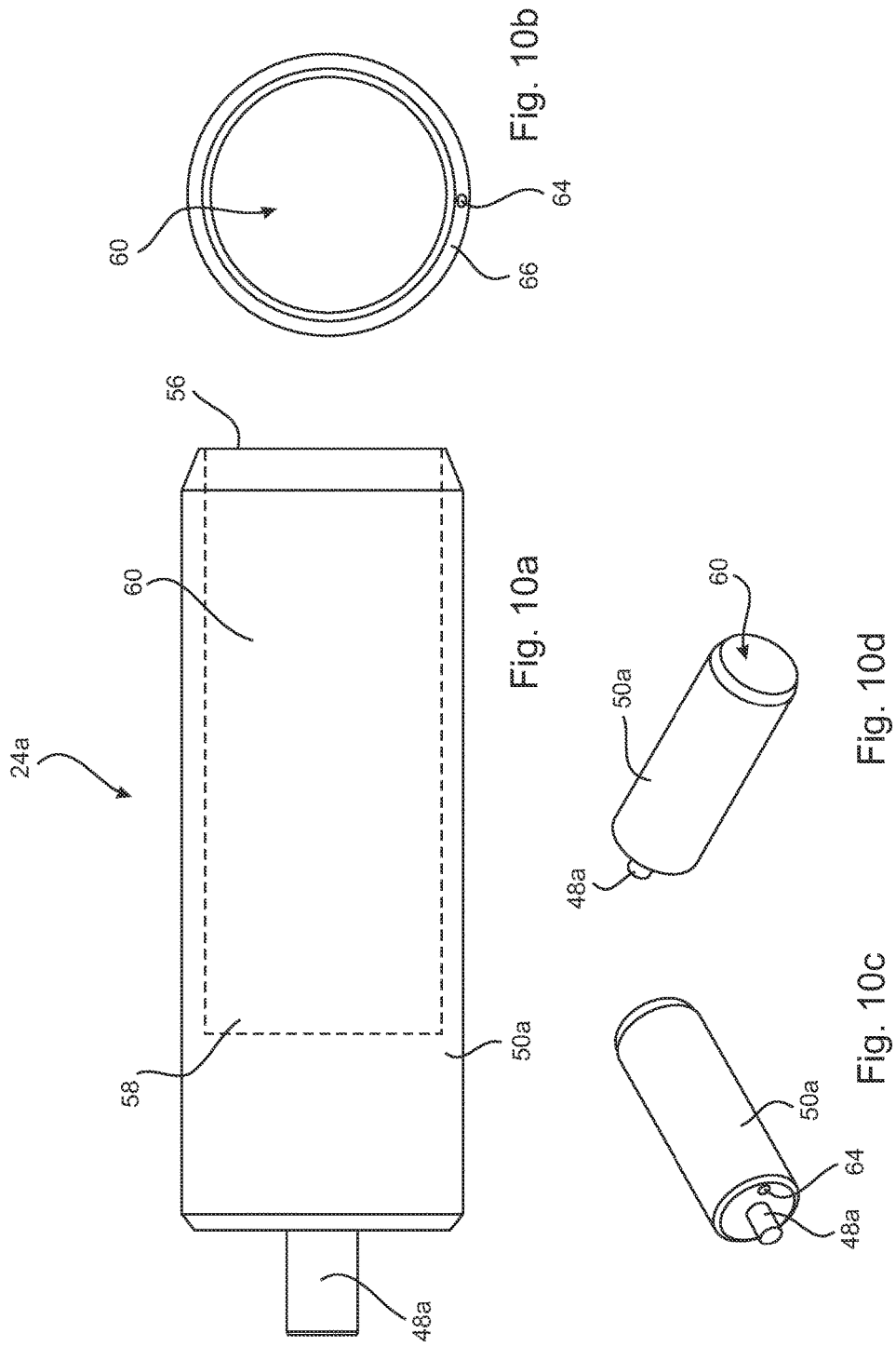

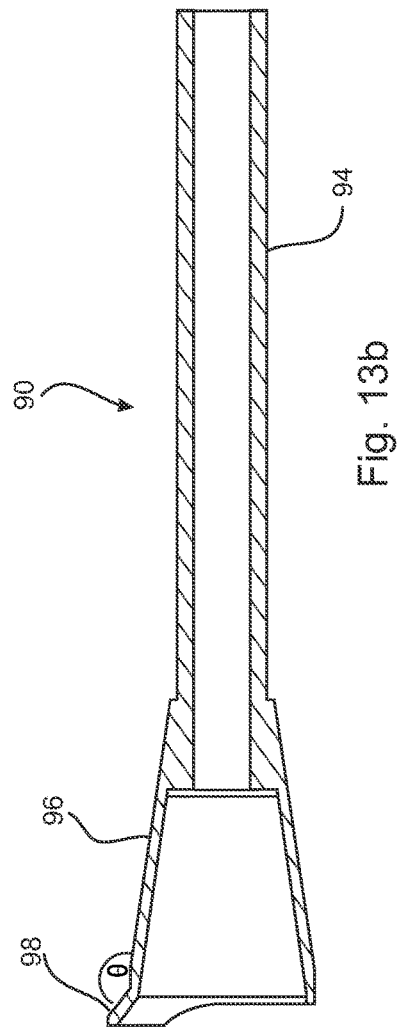
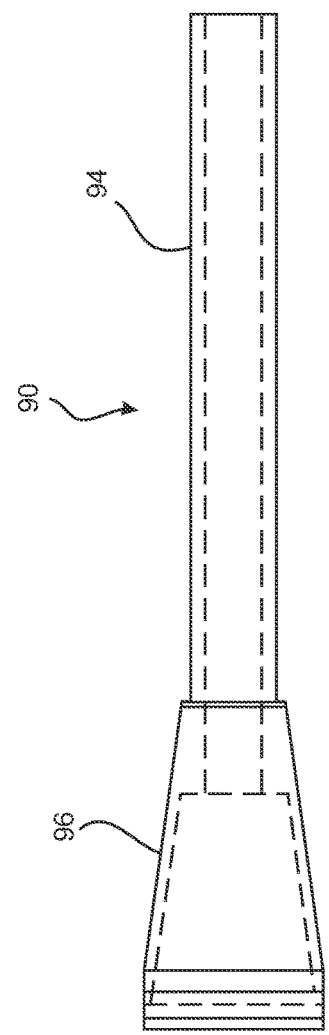
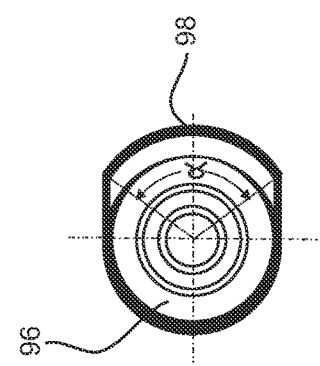

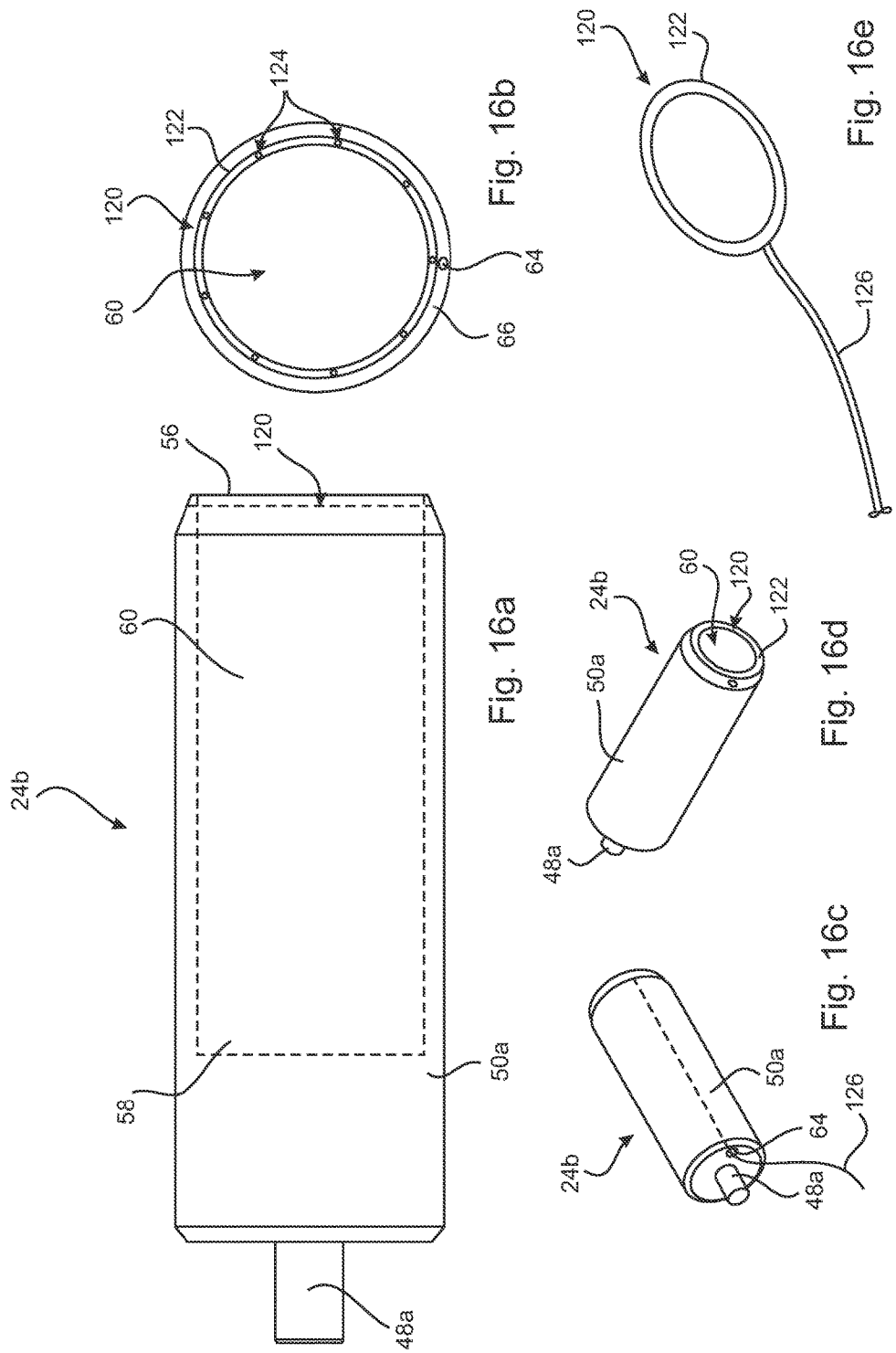

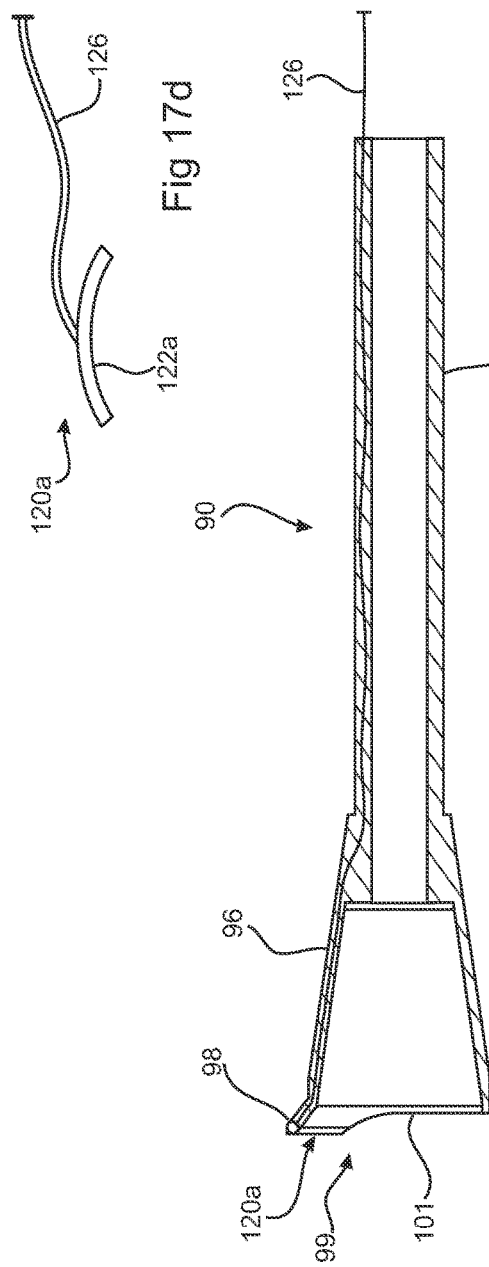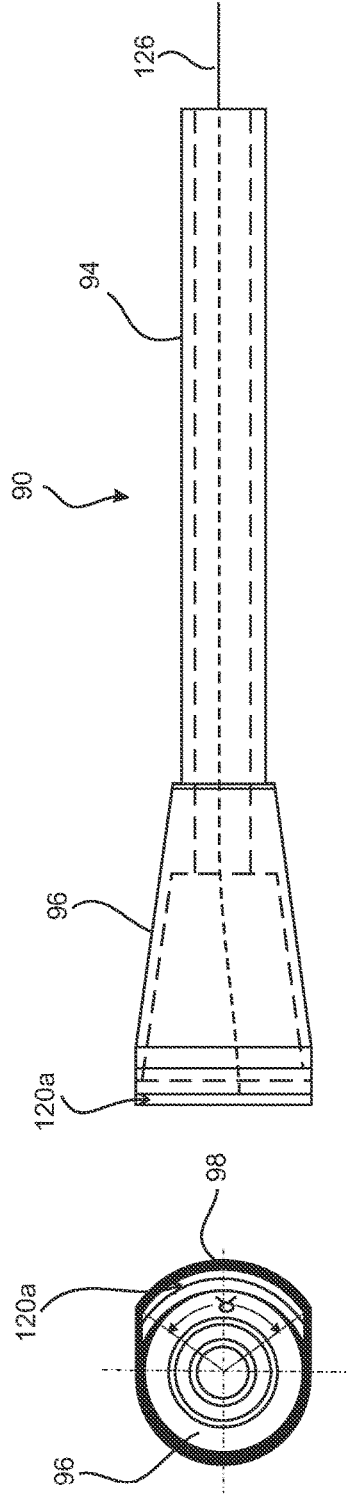

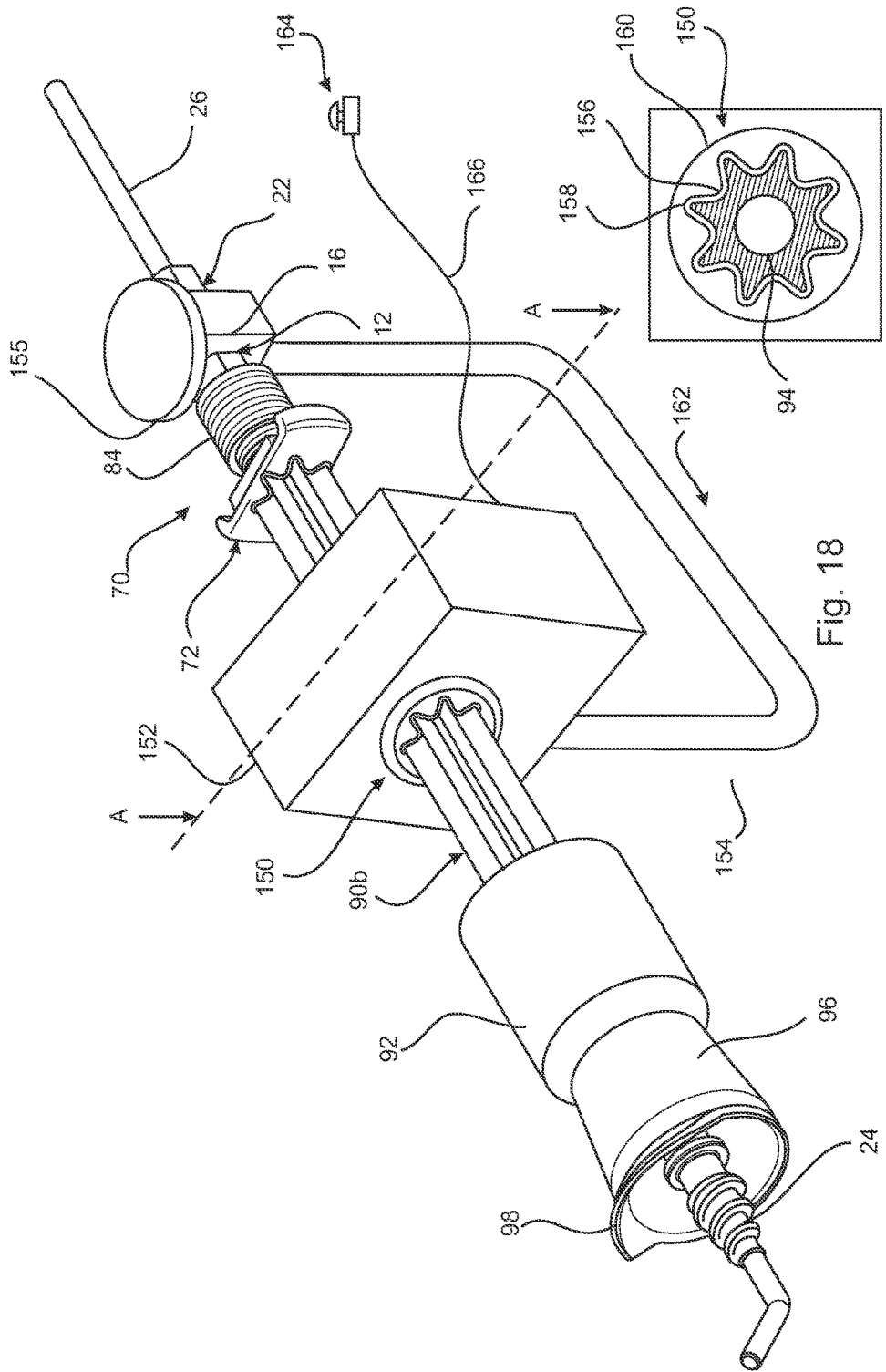

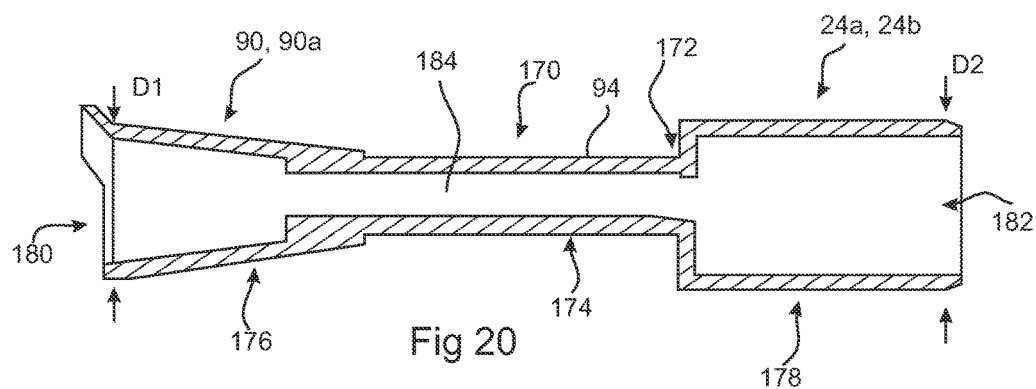
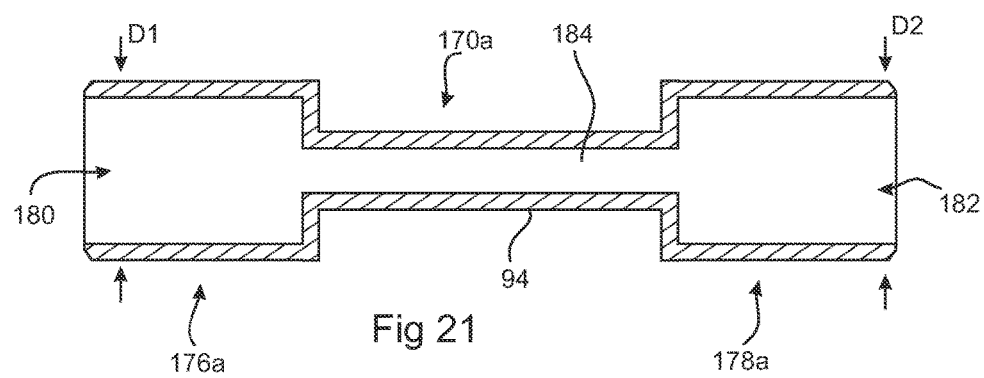
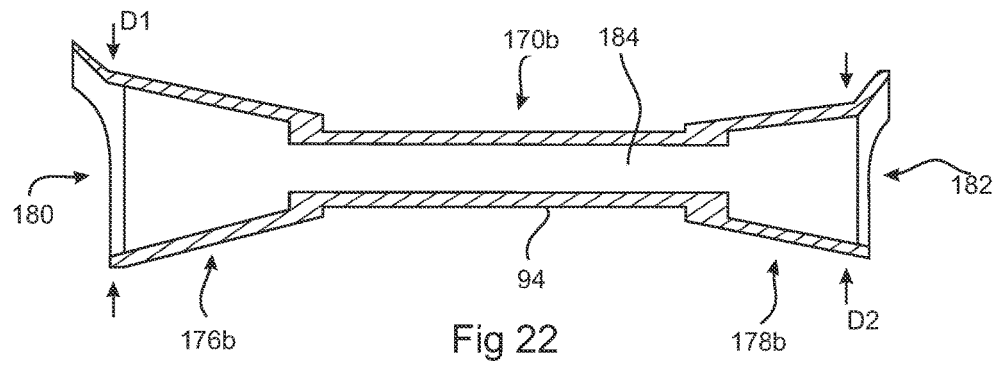

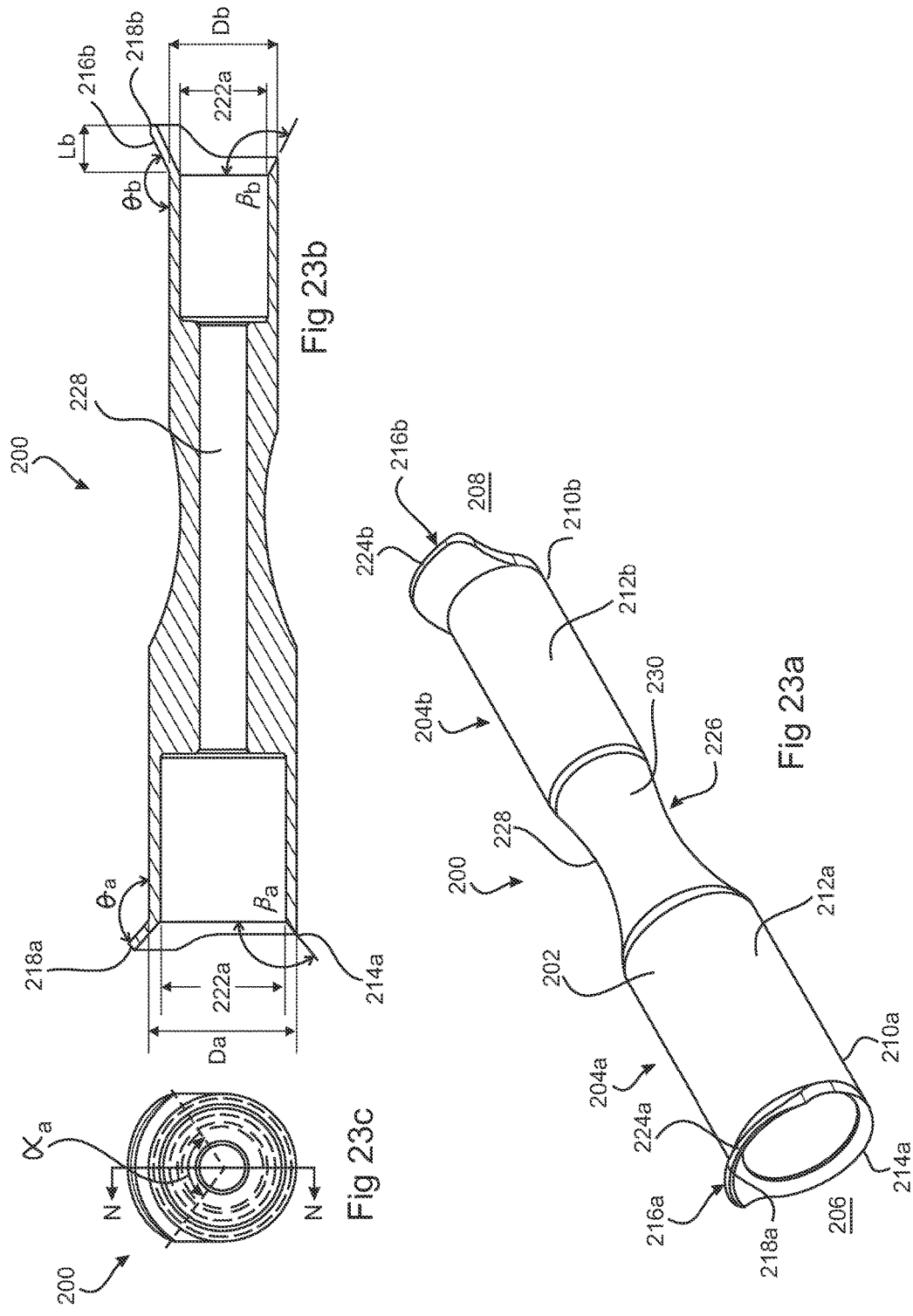

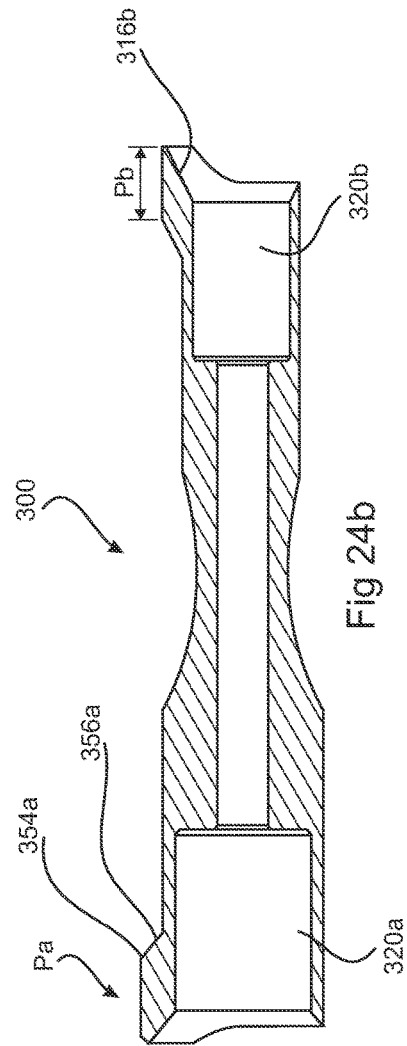
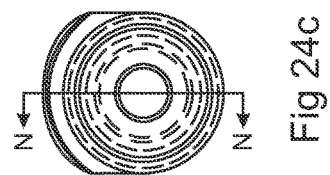
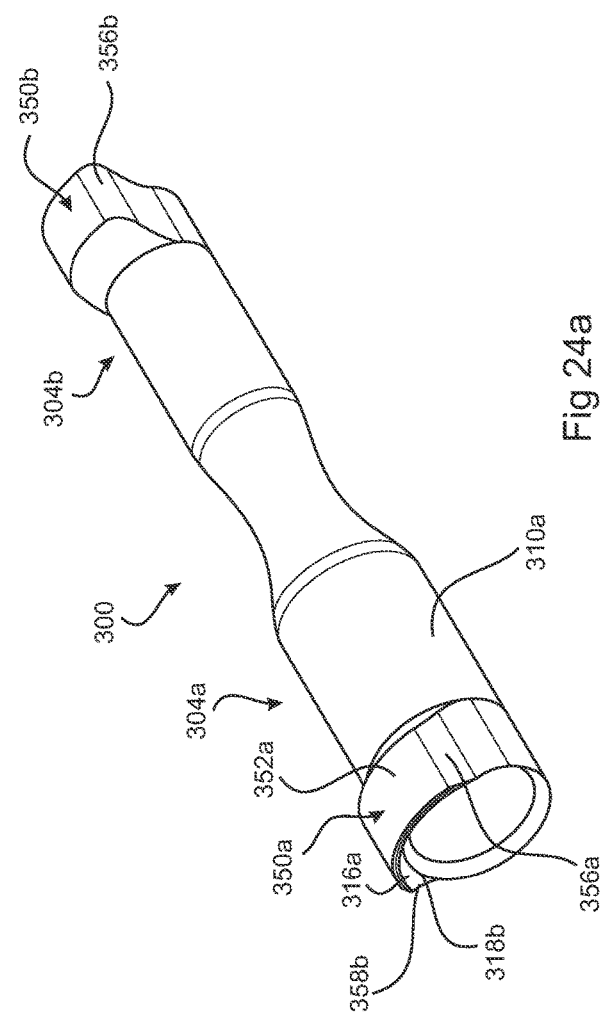

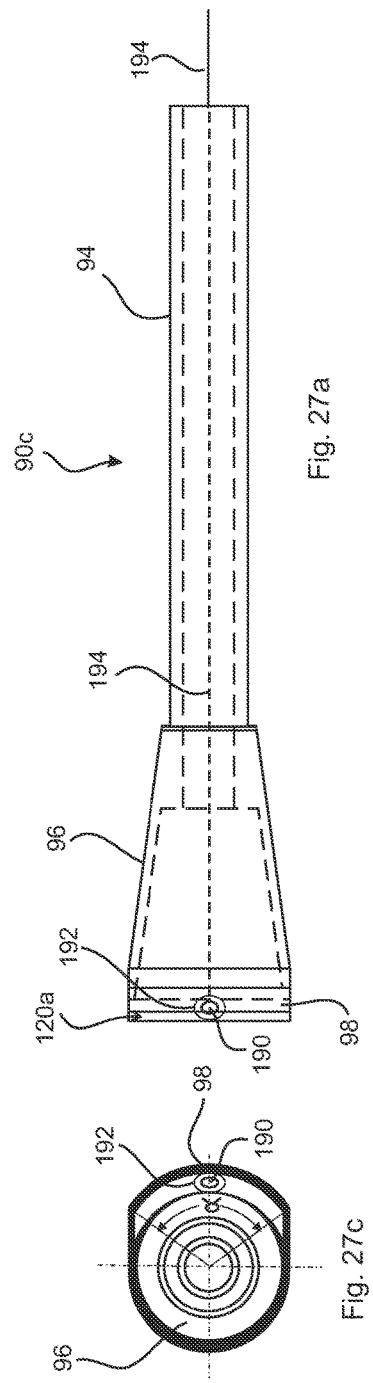

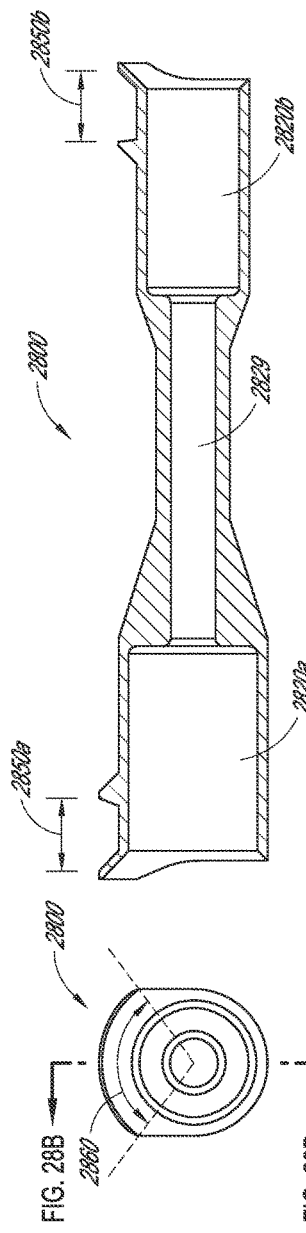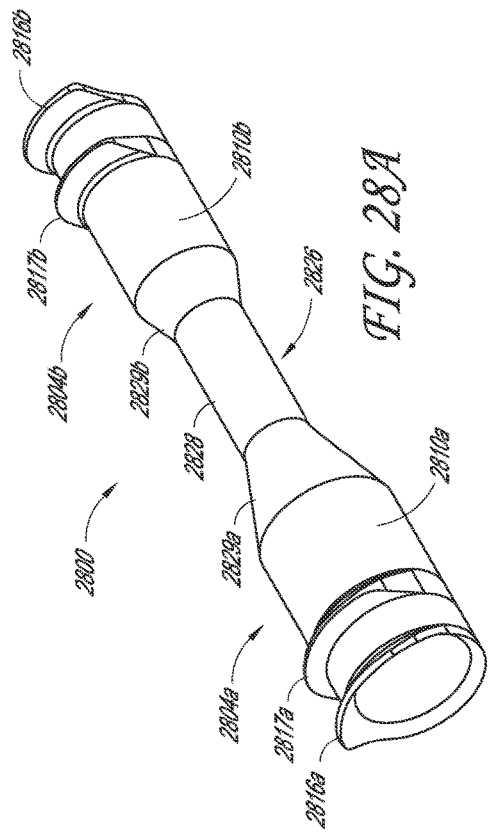

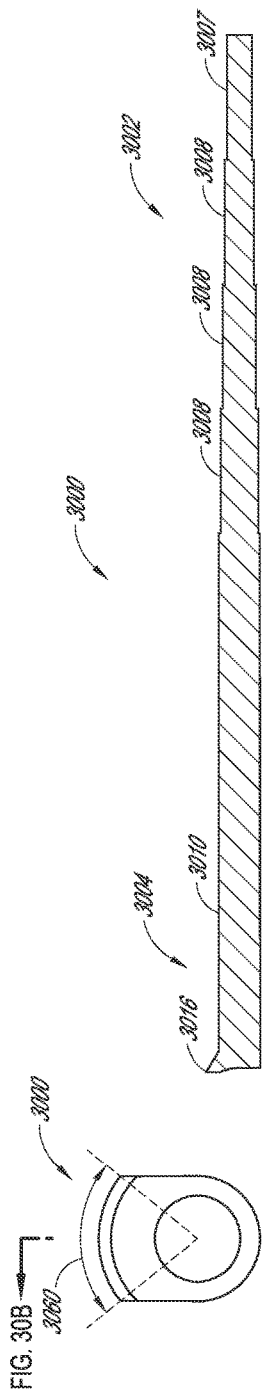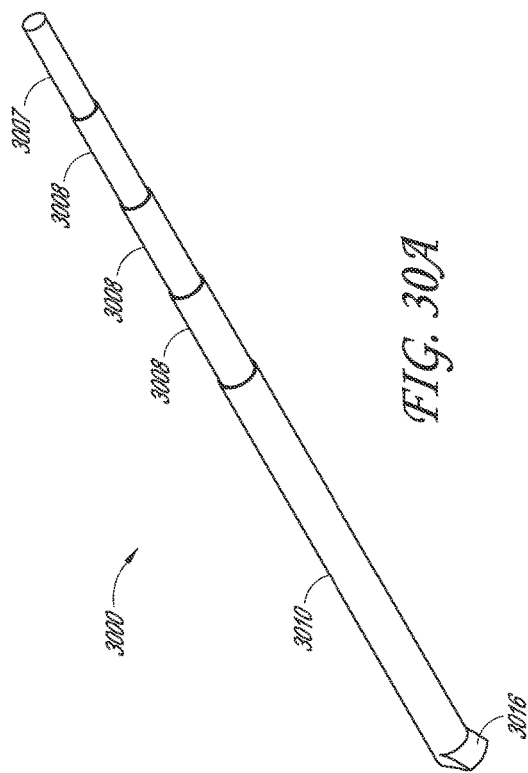

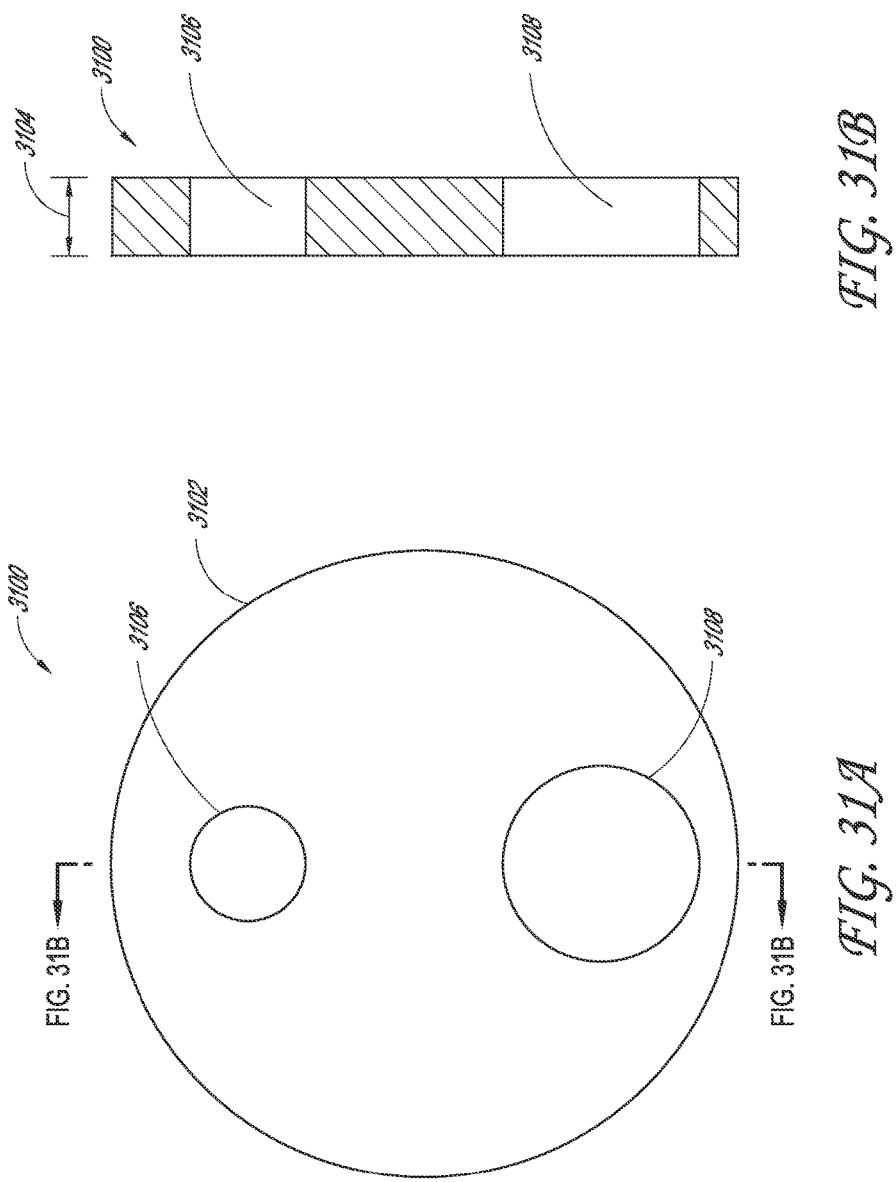

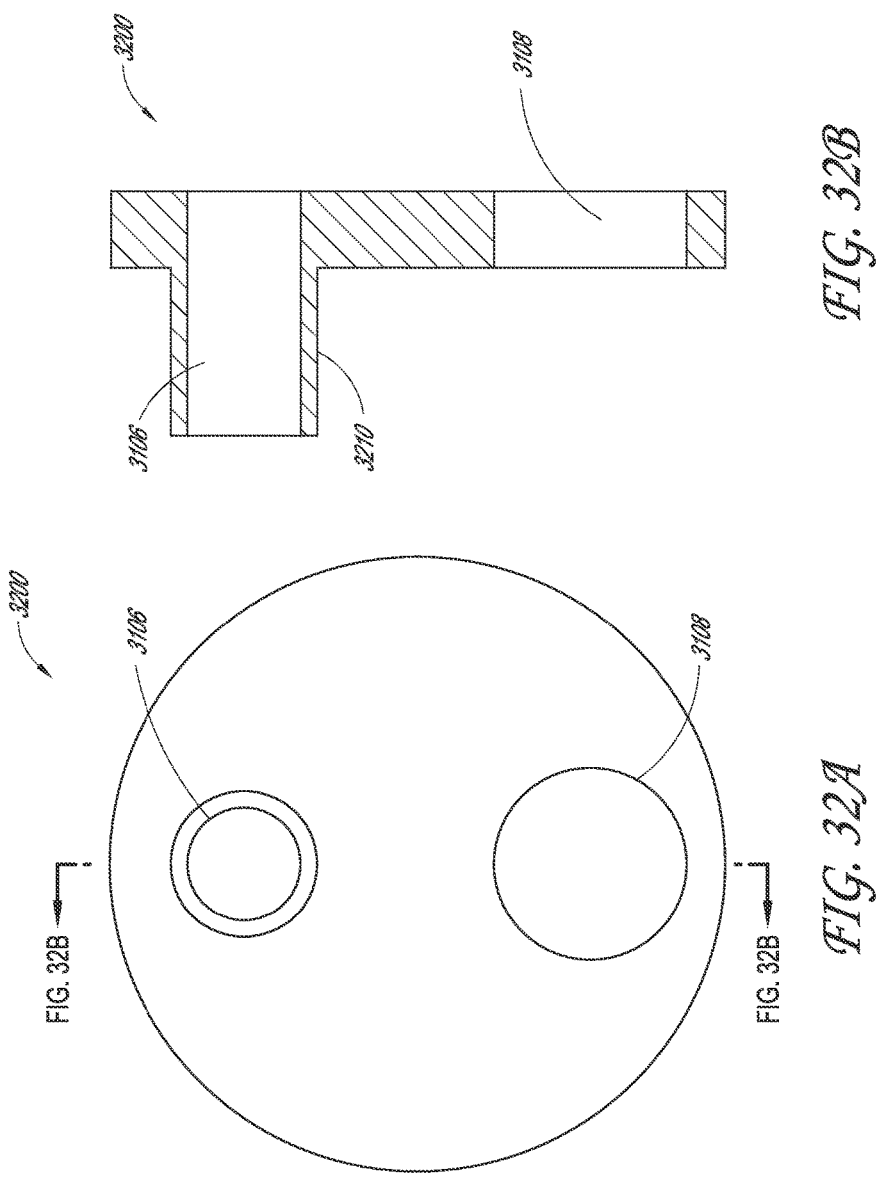

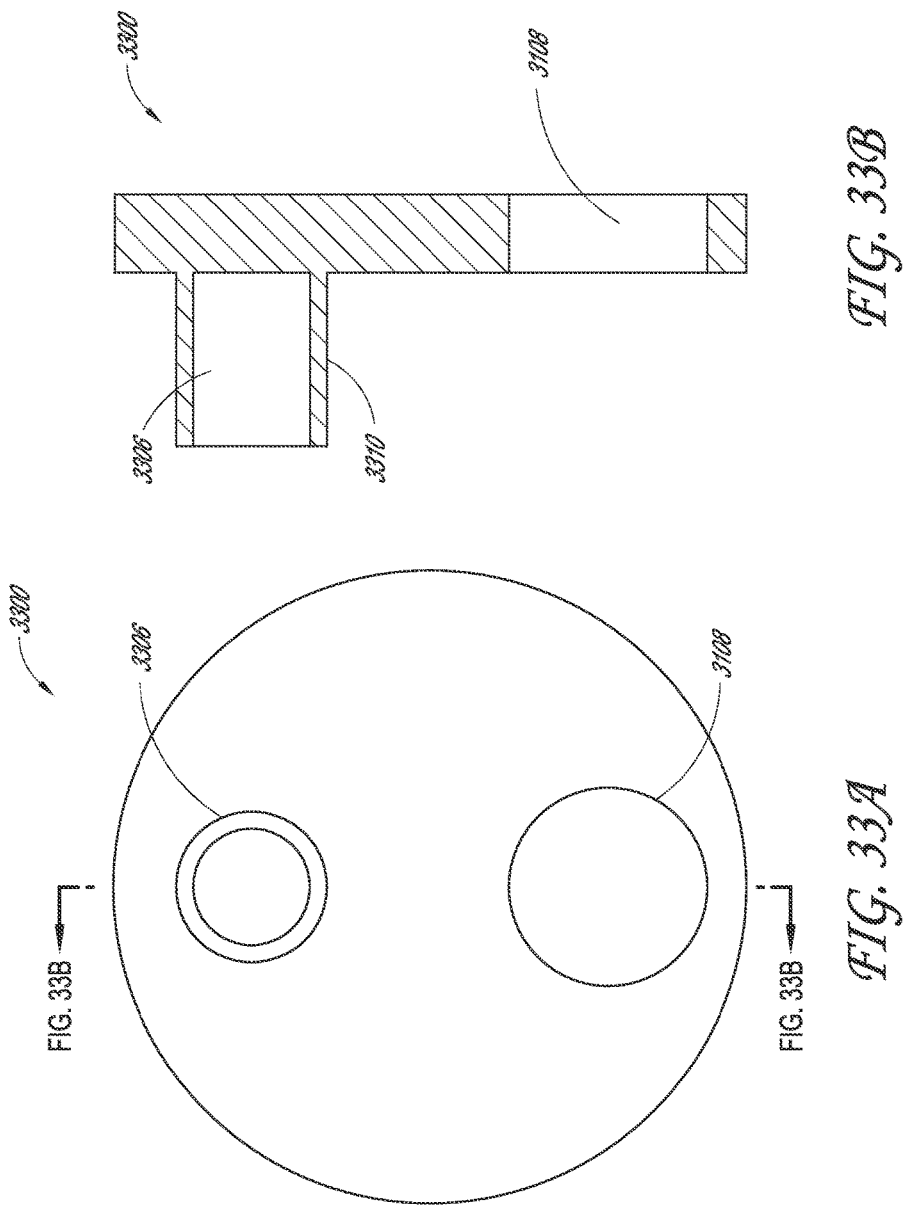

GENERAL UTERINE MANIPULATOR AND SYSTEM

CROSS-REFERENCE TO RELATED APPLICATIONS

This application is a continuation of U.S. Application Ser. No. 14/498,166, filed Sep. 26, 2014, now U.S. Pat. No. 9,101,390, which is a continuation of PCT Application No. PCT/US2013/061180, filed Sep. 23, 2013, which is a continuation-in-part of U.S. application Ser. No. 13/720,086, filed Dec. 19, 2012, which is a continuation-in-part of U.S. application Ser. No. 13/625,255, filed Sep. 24, 2012, which is a continuation-in-part of PCT Application No. PCT/AU2012/000332, filed Mar. 30, 2012, which claims the benefit of U.S. Provisional Application No. 61/472,705, filed Apr. 7, 2011. Each of the foregoing applications is hereby incorporated herein by reference in its entirety.

BACKGROUND

Field

The present disclosure relates to a general uterine manipulator and system which may be used in general surgery, gynaecological or non-surgical procedures.

Description

The present inventor has invented numerous medical instruments which are currently in use in surgical and non-surgical procedures. One such instrument is described in International publication no. WO 2008/074054 which is used in various procedures including total laparoscopic hysterectomy. The instrument described in this publication comprises a tube provided with an integral funnel at one end and through which a uterine cannula can be inserted. Both the tube and the cannula are provided with longitudinal slots or cut outs that aid in visualising the rotational position of a distal end of the instrument when inserted into the vagina and also aid in gripping of the instrument.

The success and efficacy of the above described and other instruments developed by the present inventor together with the need for improved and more versatile instruments have led to the present disclosure.

SUMMARY

According to one aspect of the present disclosure there is provided a general uterine manipulator comprising:

an elongated hollow tube defining an internal passage and having opposite first and second ends;

a smooth continuous outer surface of constant outer diameter extending between the first and second ends; and, internal first and second screw threads formed in the elongated hollow tube, the first screw thread being formed at the first end and the second screw thread being formed at the second end.

The general uterine manipulator may comprise a first fitting having a screw thread arranged to engage the first screw thread, the first fitting also having an axial through hole and configured to receive an inner manipulator shaft.

In some embodiments the first fitting is configured to apply increasing clamping force on a received inner manipulator when the first fitting a screw further into the first end.

The general uterine manipulator may comprise a hydrotubation port in fluid communication with the internal passage wherein a fluid injected into or through the hydrotubation port is able to flow into the internal passage.

In some embodiments the hydrotubation port is formed in the elongated hollow tube at a location near the first end and beyond the first screw thread.

In some embodiments the hydrotubation port is formed in the first fitting and is in fluid communication with the axial through hole.

The axial through hole may comprise a first length which opens onto an end of the first fitting distant the screw thread of the first fitting, and a second contiguous length wherein the first length has a first internal diameter and the second length has a second internal diameter which is greater than the first internal diameter; and wherein the hydrotubation port opens onto the second length of the axial through hole.

The general uterine manipulator may comprise a second fitting having a threaded portion provided with a screw thread configured to engage the second internal thread on the elongated hollow tube and a body portion extending co-linearly from the threaded portion.

In some embodiments the body portion comprises a tubular member which is open at one end distal the threaded portion and is closed at an end near to the threaded portion to form a cavity.

In some embodiments the tubular member comprises a circumferential wall and at least one internal passage formed in the circumferential wall, the or each internal passage opening onto axially opposite ends of the circumferential wall.

In some embodiments the body portion comprises a conically shaped portion with decreasing outer diameter in a taper direction being away from the threaded portion and wherein the conically shaped portion is provided with an external coarse screw thread.

In some embodiments the second fitting is provided with an axial through hole.

The general uterine manipulator may comprise an inner manipulator shaft, the shaft capable of being received in the axial through hole of the first fitting and the axial through hole of the second fitting and extending through the internal passage.

In some embodiments a crest of the coarse screw thread is provided with a flattened surface wherein a line on the flattened surface is inclined relative to a central axis of the coarse screw thread in the taper direction.

In some embodiments the coarse screw thread is a ball screw thread.

In some embodiments the general uterine manipulator comprising a forceps holder supported on the elongated hollow tube and configured to be releasably lockable in a plurality of positions along the elongated hollow tube.

In some embodiments the forceps holder comprises a first component seated on the elongated hollow tube and provided with a detent for gripping a finger hole of the forceps.

In some embodiments the forceps holder comprises a locking nut engagable with the first component and arranged to releasably lock the first component in a fixed position along the elongated hollow tube when rotated in a first direction, and to release the second component to allow sliding motion along the elongated hollow tube when rotated in an opposite direction.

In a second aspect there is provided general uterine manipulator comprising:

an elongated hollow tube defining an internal passage and having opposite first and second ends;

a smooth continuous outer surface of constant outer diameter extending between the first and second ends;

internal first and second screw threads formed in the elongated hollow tube, the first screw thread being formed at the first end and the second screw thread being formed at the second end;

a first fitting having a screw thread arranged to engage the first screw thread, the first fitting also having an axial through hole;

a second fitting having a threaded portion provided with a screw thread configured to engage the second internal thread on the elongated hollow tube and a body portion extending co-linearly from the threaded portion; and, an inner manipulator shaft arranged to extend through the axial through hole, the internal passage and the second fitting, the inner manipulator shaft having one end which is bent and protrudes from the second fitting.

In one embodiment the general uterine manipulator comprises a resistance mechanism enabling the axial and rotational position of the inner manipulator shaft to substantially held in the absence of adjustment by a user of the manipulator.

In one embodiment the resistance mechanism comprises clamp shells incorporated in the first fitting.

In one embodiment the resistance mechanism comprises a bend in a portion of the inner manipulator shaft within the internal passage the bend being to an extent that the inner manipulator shaft bears against an inside surface of the tube.

In one embodiment the general uterine manipulator comprises a hydrotubation port formed in the first fitting and in fluid communication with the axial through hole wherein a fluid injected into or through the hydrotubation port is able to flow into the internal passage. In this embodiment the axial through hole comprises a first length which opens onto an end of the first fitting distant the screw thread of the first fitting, and a second contiguous length wherein the first length has a first internal diameter and the second length has a second internal diameter which is greater than the first internal diameter; and the hydrotubation port opens onto the second length of the axial through hole.

In one embodiment the second fitting comprises a threaded portion provided with a screw thread configured to engage the second internal thread on the elongated hollow tube and a body portion extending co-linearly from the threaded portion, the body portion having a frusto-conical shape with decreasing outer diameter in a direction away from the threaded portion and on which is provided an external coarse screw thread.

In one embodiment the general uterine manipulator comprises a forceps holder supported on the elongated hollow tube and configured to be releasably lockable in a plurality of positions along the elongated hollow tube.

In one embodiment the forceps holder comprises a first component seated on the elongated hollow tube and provided with a detent for gripping a handle of the forceps.

In one embodiment the forceps holder comprises a locking nut engagable with the first component and arranged to releasably lock the first component in a fixed position along the elongated hollow tube when rotated in a first direction, and to release the second component to allow sliding motion along the elongated hollow tube when rotated in an opposite direction.

In one embodiment the general uterine manipulator comprises a cervical funnel mounted on the tube.

In a third aspect there is provided a general uterine manipulator system comprising:

an elongated hollow tube defining an internal passage and having opposite first and second ends;

a smooth continuous outer surface of constant outer diameter extending between the first and second ends;

internal first and second screw threads formed in the elongated hollow tube, the first screw thread being formed at the first end and the second screw thread being formed at the second end;

at least one first fitting the or each first fitting having a screw thread arranged to engage the first screw thread, the first fitting also having an axial through hole;

at least one second fitting the or each second fitting having a threaded portion provided with a screw thread configured to engage the second internal thread on the elongated hollow tube and a body portion extending co-linearly from the threaded portion;

wherein the at least one first fitting comprises one or both of: (a) a clamping first fitting configured to apply increasing clamping force on a received inner manipulator when the first fitting a screw further into the first end; and (b) a hydrotubation first fitting which has a hydrotubation port in fluid communication with the internal passage wherein a fluid injected into or through the hydrotubation port is able to flow into the internal passage; and wherein the at least one second fitting comprises one or both of: (c) a cervical second fitting in which its body portion is of a frusto-conical shape with decreasing outer diameter in a direction away from the threaded portion and is provided with an external coarse screw thread; and (d) a tubular second fitting in which its body portion comprises a tubular member which is open at one end distal the threaded portion of the second fitting and is closed at an end near to the threaded portion of the second fitting to form a cavity.

In one embodiment the tubular member of the tubular second fitting comprises a circumferential wall and at least one internal passage formed in the circumferential wall, the or each internal passage opening onto axially opposite ends of the circumferential wall.

In one embodiment the general uterine manipulator system comprises an inner manipulator shaft arranged to extend through the axial through hole, the internal passage and the second fitting when the second fitting is the cervical second fitting, the inner manipulator shaft having one end which is bent and protrudes from the cervical.

In one embodiment the general uterine manipulator system a resistance mechanism enabling the axial and rotational position of the inner manipulator shaft to substantially held in the absence of adjustment by a user.

In one embodiment the general uterine manipulator system a forceps holder supported on the elongated hollow tube and configured to be releasably lockable in a plurality of positions along the elongated hollow tube.

In a fourth aspect there is provided a medical instrument configured to facilitate a gynaecological procedure comprising:

a body provided with opposite first and second end portions, the first end portion having a first opening and the second end portion having a second opening;

a throughway extending between the first and second openings, the throughway arranged to enable the body to be supported on a shaft to facilitate insertion of one of the first and second end portions into a body cavity.

In one embodiment the first and second end portions are different in one or more of their shape, size and configuration.

In one embodiment the first end portion is of a tubular configuration and has a first outer diameter.

In one embodiment the second end portion is of a tubular configuration and has a second outer diameter that is different to the first outer diameter.

In one embodiment the second end portion is of a frusto conical configuration.

In one embodiment the first end portion is of a frusto conical configuration and has a first outer diameter.

In one embodiment the second end portion is of a frusto conical configuration and has a second outer diameter that is different to the first outer diameter.

In one embodiment the or each end portion of frusto conical configuration is provided with a lip that extends radially outward from an outer surface of the second end portion and for an arc of less than 360°.

In one embodiment one or both of the first and second end portions is provided with an illumination device arranged to enable the emission of light from the respective end portion.

In one embodiment the device comprises an illumination device arranged to enable the emission of light from the lip.

In one embodiment the general uterine manipulator system comprises an illumination device arranged to enable the emission of light from an end of the tubular portion.

In one embodiment the general uterine manipulator system comprises an illumination device arranged to enable the emission of light from an end of the cervical funnel.

In one embodiment the general uterine manipulator system comprises an illumination device arranged to enable the emission of light from an end of the tubular second fitting.

In one embodiment the general uterine manipulator system comprises a motor arranged to engage and rotate the cervical funnel.

In one embodiment the general uterine manipulator system comprises a foot operated switch associated with the motor and switchable between a first position wherein the motor rotates in a clockwise direction and a second position wherein the motor rotates in an anti-clockwise direction.

In one embodiment the cervical funnel has conical portion and a through hole formed in or near a large diameter end the conical portion.

In one embodiment the large diameter end of the conical portion has an outwardly flared lip that extend for a part of the circumference of the conical portion and wherein the hole is formed in the lip.

In one embodiment the general uterine manipulator system comprises an illumination device arranged to illuminate the through hole.

In a fifth aspect there is provided a cervical funnel comprising a conical portion and a through hole formed in or near a large diameter end the conical portion.

In one embodiment the funnel comprises the large diameter end of the conical portion has an outwardly flared lip that extend for a part of the circumference of the conical portion and wherein the hole is formed in the lip.

In one embodiment the funnel comprises an illumination device arranged to illuminate the through hole.

In one embodiment the illumination device comprises an annular light guide surrounding the through hole.

In a sixth aspect there is provided a cervical funnel comprising a conical portion and a tube extending coaxially form a small diameter end of the conical portion, wherein an outer surface of the tube is profiled to mechanically engage a motor to facilitate rotation of the cervical funnel.

In one embodiment the outer surface of the tube is provided with gear teeth arranged to enable mechanical engagement with the motor.

In one embodiment the funnel comprises a through hole formed in or near a large diameter end the conical portion.

In one embodiment the large diameter end of the conical portion has an outwardly flared lip that extend for a part of the circumference of the conical portion and wherein the hole is formed in the lip.

In a seventh aspect there is provided a double ended medical instrument arranged for insertion into a body cavity comprising:

a body having a first probe at first end, a second probe at a second opposite end;

the first probe having a cylindrical portion with an first outer circumferential surface of a first diameter, a first circumferential edge distant the first end and a first lip projecting outwardly from the first outer circumferential surface beyond the first circumferential edge and extending for at least a part of a circumference of the first circumferential edge;

the second probe having a cylindrical portion with a second outer circumferential surface of a second outer diameter, a second circumferential edge distant the first probe and a second lip projecting outwardly from the second outer circumferential surface beyond the second circumferential edge and extending for at least a part of a circumference of the second circumferential edge;

wherein the first outer diameter and the second outer diameter are different from each other.

In one embodiment the first and second lips have respective mid-points that are located in axial alignment.

In one embodiment the part of the circumference of the first and second circumferential edges about which the first and second lips respectively extend are the same.

In one embodiment the first probe is provided with a first cavity extending axially from the first circumferential edge toward the second probe and having a first inner diameter.

In one embodiment the second probe is formed with a second cavity extending axially from the second circumferential edge toward the first probe and having a second inner diameter wherein the second inner diameter is different to the first inner diameter.

In one embodiment the first probe is provided with a first platform of constant first outer diameter extending over the first cylindrical portion from a circumferential edge of the first lip toward the second probe.

In one embodiment the first platform is co-extensive in a circumferential aspect with the first lip.

In one embodiment a side of the first platform rearward of the first lip slopes from the first outer diameter to first outer circumferential surface in a direction toward the second probe.

In one embodiment circumferentially opposite sides the first platform transition smoothly from first outer diameter the first outer circumferential surface.

In one embodiment the second probe is provided with a second platform of constant second outer diameter extending over the second cylindrical portion from a circumferential edge of the second lip toward the first probe.

In one embodiment the second platform is co-extensive in a circumferential aspect with the second lip.

In one embodiment a side of the second platform rearward of the second lip slopes from the second outer diameter in a direction toward the first probe.

In one embodiment circumferentially opposite sides the second platform transition smoothly from second outer diameter the second outer circumferential surface.

In one embodiment the platform has a circumferential surface of constant diameter extending coaxially with the first outer circumferential surface.

In one embodiment the double ended medical instrument comprises an intermediate portion that transitions smoothly between the first and second probes.

In one embodiment the intermediate portion has a central region of an outer diameter less than each of the first diameter and the second outer diameter.

In one embodiment the double ended medical instrument comprises an intermediate portion that transitions smoothly between the first and second probes wherein the intermediate portion is formed with an internal bore the bore extending in an axial direction between the first and second cavities and having an inner diameter smaller than each of the first and second inner diameters.

In one embodiment the first lip and second lip extend for the full circumference of first circumferential edge and the second circumferential edge respectively; the first probe being provided with a first platform of constant first outer diameter extending wholly about the first cylindrical portion from a circumferential edge of the first lip toward the second probe; and the second probe being provided with a second platform of constant second outer diameter extending wholly about the second cylindrical portion from a circumferential edge of the second lip toward the first probe.

In an eighth aspect there is provided a medical instrument configured to be inserted into a body cavity, the medical instrument comprising: a body comprising a first probe at a first end, the first probe comprising: a first cylindrical portion with a first outer circumferential surface of a first diameter; a first circumferential edge at a distal end of the first probe; a first distal lip projecting outwardly from the first outer circumferential surface beyond the first circumferential edge and extending for at least a part of a circumference of the first circumferential edge; and a first marker lip projecting outwardly from the first outer circumferential surface and extending for at least a part of a circumference of the first outer circumferential surface; wherein the first distal lip is positioned distal to the first marker lip; and wherein the body comprises a hollow cavity to enable a second medical instrument to pass therethrough.

In some embodiments, the body further comprises: a second probe at a second end, the second probe comprising: a second cylindrical portion with a second outer circumferential surface of a second diameter; a second circumferential edge at a distal end of the second probe; a second distal lip projecting outwardly from the second outer circumferential surface beyond the second circumferential edge and extending for at least a part of a circumference of the second circumferential edge; and a second marker lip projecting outwardly from the second outer circumferential surface and extending for at least a part of a circumference of the second outer circumferential surface; wherein the second distal lip is positioned distal to the second marker lip; wherein the second end is opposite the first end; and wherein the first diameter and second diameter are different from each other.

In some embodiments, the first marker lip is positioned approximately 20 millimeters in a longitudinal direction from the first distal lip.

In some embodiments, the second marker lip is positioned approximately 20 millimeters in a longitudinal direction from the second distal lip.

In some embodiments, the first marker lip and first distal lip have respective mid-points that are located in axial alignment.

In some embodiments, the second marker lip and second distal lip have respective mid-points that are located in axial alignment.

In some embodiments, the first distal lip and second distal lip have respective mid-points that are located in axial alignment.

In some embodiments, the medical instrument further comprises a pneumatic plug having a tapered surface configured to pneumatically plug at least a portion of the hollow cavity.

In some embodiments, the medical instrument further comprises an intermediate portion that transitions smoothly between the first and second probes.

In some embodiments, the medical instrument further comprises an intermediate portion positioned between the first and second probes, wherein the intermediate portion is cylindrical.

In some embodiments, the intermediate portion has a central region of an outer diameter less than each of the first diameter and second diameter.

In a ninth aspect there is provided a double ended medical instrument configured to be inserted into a body cavity, the double ended medical instrument comprising: an elongate body comprising: a first cylindrical segment positioned at a first end of the body; a second cylindrical segment positioned at a second end of the body; a first plurality of graduated cylindrical segments positioned between the first cylindrical segment and a central cylindrical segment; and a second plurality of graduated cylindrical segments positioned between the second cylindrical segment and the central cylindrical segment; wherein the first cylindrical segment, second cylindrical segment, and central cylindrical segment each have different outer diameters, with the central cylindrical segment having the largest outer diameter; wherein the first plurality of graduated cylindrical segments comprise outer diameters larger than the first cylindrical segment, but smaller than the central cylindrical segment; wherein the second plurality of graduated cylindrical segments comprise outer diameters larger than the second cylindrical segment, but smaller than the central cylindrical segment; and wherein the first cylindrical segment, second cylindrical segment, central cylindrical segment, first plurality of graduated cylindrical segments, and second plurality of graduated cylindrical segments are positioned collinearly.

In some embodiments, the first cylindrical segment comprises an outer diameter configured to be smaller than an undilated diameter of a human cervical canal.

In some embodiments, the first cylindrical segment comprises an outer diameter of approximately two millimeters.

In some embodiments, the second cylindrical segment comprises an outer diameter larger than any of the first cylindrical segment and the first plurality of graduated cylindrical segments.

In a tenth aspect there is provided a double ended medical instrument configured to be inserted into a body cavity, the double ended medical instrument comprising: a body comprising a probe at a first end, the probe comprising: a cylindrical plug portion with an outer circumferential surface of a first diameter; a circumferential edge at a distal end of the probe; and a lip projecting outwardly from the outer circumferential surface beyond the circumferential edge and extending for at least a part of a circumference of the circumferential edge; wherein the body further comprises a dilator at a second end, the second end opposite the first end, the dilator comprising: a first cylindrical segment positioned at a distal end of the dilator; and a plurality of graduated cylindrical segments positioned between the first cylindrical segment and the cylindrical plug portion of the probe, wherein the plurality of graduate cylindrical segments comprise incremental outer diameters having values larger than an outer diameter of the first cylindrical segment and smaller than the first diameter of the cylindrical plug portion; wherein the cylindrical plug portion, first cylindrical segment, and plurality of graduated cylindrical segments are positioned collinearly.

In some embodiments, the first cylindrical segment comprises an outer diameter of approximately six millimeters and the first diameter of the cylindrical plug portion is approximately ten millimeters.

In some embodiments, the first diameter of the cylindrical plug portion is of a size configured to pneumatically plug a vaginal canal of young pig.

In some embodiments, the double ended medical instrument further comprises a cylindrical disc configured to support the body, the cylindrical disc comprising: a first port extending from a front surface of the disc to a rear surface of the disc, the first port having an inner diameter of a size to enable the body to pass therethrough; and a second port extending from the front surface of the disc to the rear surface of the disc, the second port having an inner diameter of a size to enable a tail of a pig to pass therethrough to anchor the cylindrical disc in relation to the pig.

In some embodiments, the cylindrical disc further comprises a hollow tube extending from the front surface of the disc, the hollow tube positioned collinearly to the first port.

BRIEF DESCRIPTION OF THE DRAWINGS

FIG. 1a is a representation of one embodiment of a general uterine manipulator in accordance with the present invention;

FIG. 1b is a disassembled view of the general uterine manipulator depicted in FIG. 1a;

FIG. 2 is a longitudinal section view of the tube incorporated in the general uterine manipulator shown in FIGS. 1a and 1b;

FIG. 3 is an isometric view of a tail screw incorporated in the general uterine manipulator shown in FIGS. 1a and 1b;

FIG. 4 is a side view of the tail screw shown in FIG. 3;

FIG. 5 is an end view of the tail screw shown in FIG. 3;

FIG. 6 is an isometric view of a second form of tail screw that may be incorporated in the general uterine manipulator shown in FIGS. 1a and 1b;

FIG. 7 is a side view of the tail screw shown in FIG. 6;

FIG. 8 is an end view of the tail screw shown in FIG. 6;

FIG. 9a is a side view of a second fitting incorporated in the general uterine manipulator shown in FIGS. 1a and 1b;

FIG. 9b is a longitudinal section view of the second fitting shown in FIG. 9a;

FIG. 9c is an isometric representation of the second fitting;

FIG. 10a is a side view of a second form of setting fitting that may be incorporated in the general uterine manipulator depicted in FIGS. 1a and 1b;

FIG. 10b is an end view of the second fitting shown in FIG. 9a;

FIG. 10c is an isometric view from one end of the second fitting;

FIG. 10d is a isometric view from an opposite angle of the second fitting;

FIG. 13b is a longitudinal section view of the cervical funnel;

FIG. 13c is an end view of the cervical funnel shown in FIGS. 13a and 13b;

FIG. 14b is a section view of the vaginal plug shown in FIG. 14a;

FIG. 16a is a side view of a further from of second fitting that may be incorporated in the general uterine manipulator depicted in FIGS. 1a and 1b;

FIG. 16b is an end view of the second fitting shown in FIG. 16a;

FIG. 16c is an isometric view from a first angle of the second fitting shown in FIG. 16a;

FIG. 16d is a isometric view from a second angle of the second fitting shown in FIG. 16a;

FIG. 16e is a schematic representation of an illumination device incorporated in the second fitting shown in FIG. 16a;

FIG. 17a is a side view of a cervical funnel with an illumination device incorporated in a further embodiment of the general uterine manipulator;

FIG. 17b is a longitudinal section view of the cervical funnel shown in FIG. 17a;

FIG. 17c is an end view of the cervical funnel shown in FIGS. 17a and 17b

FIG. 17d is a schematic representation of the illumination device incorporated in the cervical funnel shown in FIGS. 17a and 17b;

FIG. 18 is an isometric view of the general uterine manipulator shown in FIG. 12 but modified with the inclusion of a drive to enable powered rotation of an associated cervical funnel;

FIG. 19 is view of cross section A-A of the manipulator shown in FIG. 18;

FIG. 20 is a schematic representation of a medical instrument that can be incorporated in or used with an embodiment of the general uterine manipulator;

FIG. 21 is a schematic representation of an alternate medical instrument that can be incorporated in or used with an embodiment of the general uterine manipulator;

FIG. 22 is a schematic representation of a further form of medical instrument that can be incorporated in or used with an embodiment of the general uterine manipulator;

FIG. 23a is an isometric view of a double ended medical instrument that can be incorporated in or used with an embodiment of a general uterine manipulator;

FIG. 23b is a longitudinal section view of the instrument shown in FIG. 23a;

FIG. 23c is an end view of the instrument shown in FIG. 23a;

FIG. 24a is an isometric view of a further double ended medical instrument that can be incorporated in or used with an embodiment of a general uterine manipulator;

FIG. 24b is a longitudinal section view of the instrument shown in FIG. 24a;

FIG. 24c is an end view of the instrument shown in FIG. 24a;

FIG. 24d is an enlarged view of an extended probe that can be incorporated in the instrument shown in FIG. 24a;

FIG. 27a is a side view of a further embodiment cervical funnel with an illumination device that may be used with the general uterine manipulator;

FIG. 27b is a longitudinal section view of the cervical funnel shown in FIG. 27a;

FIG. 27c is an end view of the cervical funnel shown in FIGS. 27a and 27b; and

FIG. 27d is a schematic representation of a lip portion of the cervical funnel shown in FIGS. 27a and 27b.

FIG. 28A illustrates a perspective view of an embodiment of a double ended medical instrument.

FIG. 28B illustrates a side cross sectional view of the double ended medical instrument of FIG. 28A.

FIG. 28C illustrates a front view of the double ended medical instrument of FIG. 28A.

FIG. 30A illustrates a perspective view of an embodiment of another double ended medical instrument.

FIG. 30B illustrates a side cross sectional view of the double ended medical instrument of FIG. 30A.

FIG. 30C illustrates a front view of the double ended medical instrument of FIG. 30A.

FIG. 31A illustrates a front view of an embodiment of a medical instrument support.

FIG. 31B illustrates a side cross sectional view of the medical instrument support of FIG. 31A.

FIG. 32A illustrates a front view of another embodiment of a medical instrument support.

FIG. 32B illustrates a side cross sectional view of the medical instrument support of FIG. 32A.

FIG. 33A illustrates a front view of another embodiment of a medical instrument support.

FIG. 33B illustrates a side cross sectional view of the medical instrument support of FIG. 33A.

DETAILED DESCRIPTION

Figure 11:
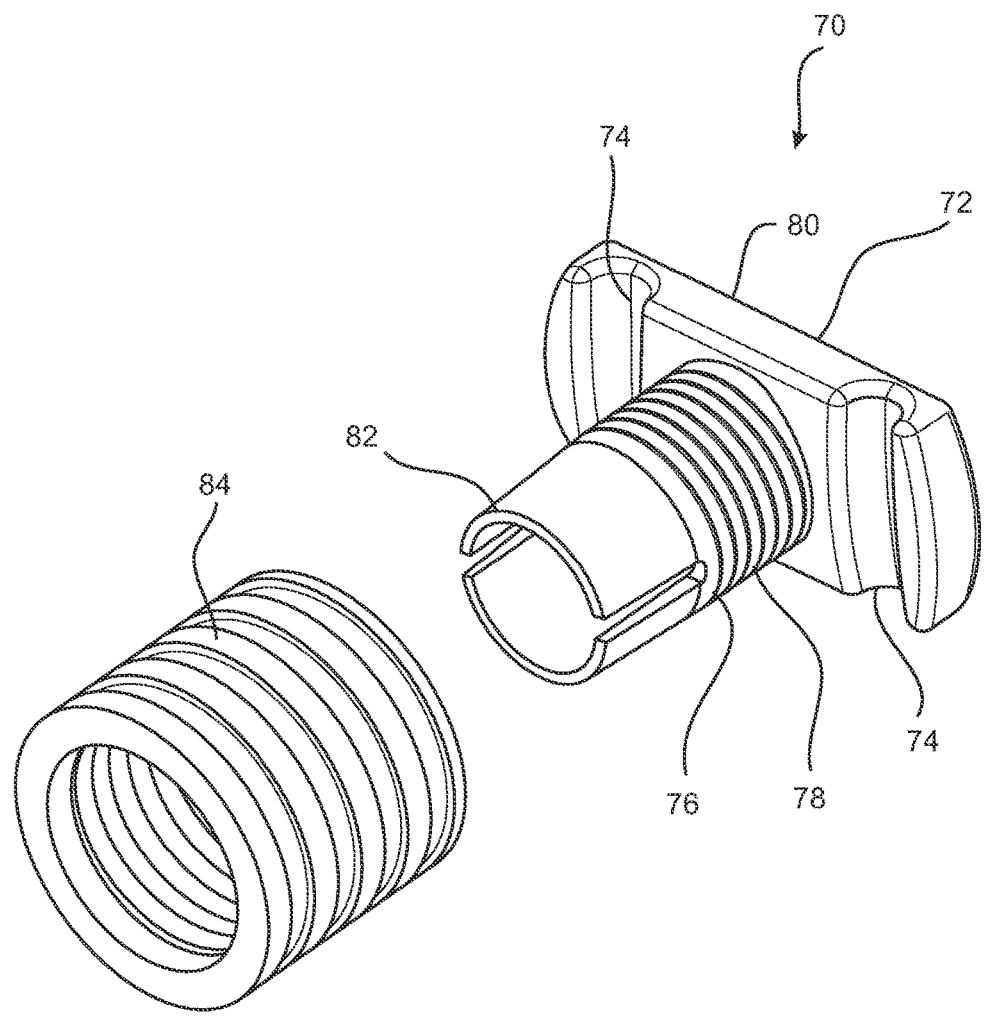
FIG. 11 is an isometric view of a forceps holder incorporated in the uterine manipulator.

Embodiments of the general uterine manipulator and associated system provide a multipurpose manipulator that may be used for a variety of procedures by interchanging particular fittings of the manipulator. With particular reference to FIGS. 1a to 2, each embodiment of the general uterine manipulator 10 (hereinafter referred to in general as "manipulator 10") is based on or incorporates an elongated hollow tube 12 defining an internal passage 14. Tube 12 has opposite first and second ends 16 and 18 and a smooth continuous outer surface 20 of constant outer diameter. A first internal screw thread T1 is formed at the first end 16 and a second internal screw thread T2 is formed at the second end 18.

The versatility of the manipulator 10 and associated system arises from the ability to connect with a number of different fittings depending on the specific application at hand. FIGS. 1a and 1b illustrate a first fitting in the form of tail screw 22 and a second fitting in the form of a cervical screw 24. An inner manipulator rod 26 is also illustrated in FIGS. 1a and 1b which extends through the first fitting 22, tube 12, and second fitting 24.

One form of the first fitting 22 is shown in greater detail in FIGS. 3 to 5. In this embodiment the first fitting 22 comprises a threaded portion 28; an integral body portion 30; and, an internal axial hole 32. Threaded portion 28 is configured to engage screw thread T1 and is provided with a transverse slot 34 terminating prior to the body portion 30. Slot 34 in effect divides the threaded portion 28 into opposed clamp shells 36a and 36b (hereinafter referred to in general as "clamp shells 36"). Body portion 30 is in the general form of a cylinder with two flats 38a and 38b on opposed sides that assist in gripping of the fitting 22. Axial hole 32 is of constant diameter for the length of the fitting 22 except for a counter sink 40 at a distal end of fitting 22.

Threaded portion 28 is slightly flared outwardly so as it is screwed into screw thread T1 at end 16, the clamp shells 36 move toward each other. When an inner manipulator rod 26 is used in the manipulator 10 this results in a clamping action on the rod providing resistance to movement of the rod 26 so as to hold it at a desired rotational and translational position. Unscrewing of the portion 28 releases or reduces this resistance to enable adjustment of the position and orientation of the rod 26. Thus the first fitting can be considered in this embodiment as incorporating or comprising a resistance mechanism which substantially maintains the position of the rod 26 until moved or adjusted by a surgeon or other user.

FIGS. 6 to 8 depict an alternate form of the first fitting denoted as 22'. Features of the fitting 22' which are of the same or similar configuration or function as those of fitting 22 are denoted with the same reference numbers but with the addition of the prime (') symbol. Fitting 22' comprises a threaded portion 28', body 30', an inner axial hole 32' with counter sink 40' at a distal end, and opposed flats 38'a and 38'b formed on body portion 30'. Fitting 22' differs from fitting 22 by the omission of slot 34, the inclusion of a hydrotubation port 42, and a re-configuring of the axial hole 32'. With particular reference to FIG. 7 it can be seen that the axial hole 32' has a first length 44 and a contiguous second length 46. The first length 44 extends from the threaded portion 28' for a majority of the axial length of fitting 22'. The second length 46 extends between and joins the counter sink 40' to the first length 44. The inner diameter of the first length 44 is greater than the inner diameter of second length 46'. Further, the inner diameter of second length 46 is dimensioned to be slightly greater than an outer diameter of the inner manipulator rod 26 forming a close fit but enabling the rod 26 to pass through the axial hole 32'.

Hydrotubation port 42 is formed in the body 30' at a location where it communicates with the first length 44. The thread on threaded portion 28' is arranged to engage with the thread T1 at end 16. In the event that for example the manipulator 10 is being used in a gynaecological application and it is desired to inject a liquid such as a dye to assist in the visualisation of tissue the dye may be injected through the hydrotubation port 42. The dye then flows through the internal passage 14 and from an opposite end of second fitting 24 attached to end 18. In this regard in the event that manipulator rod 26 is in use, a clearance exists between second fitting 24 and an outer surface of rod 26 to allow the flow of dye or other fluid. Further, the close fitting between the rod 26 and second length 46 of axial hole 32' substantially prevents any back leakage of the dye. Alternately and/or in addition if desired, a rubber grommet seal (not shown) may be provided in the second length 46 to further minimize back leakage of dye or other liquid injected through the hydrotubation port 42.

As the fitting 22' does not have the clamping shells 36 of fitting 22 it is unable to clamp inner manipulation rod 26. However in embodiments of the manipulator 10, the inner manipulator rod 26 can be bent to varying degrees intermediate of its length so that the rod 26 bears against an inside surface of tube 12 to provide resistance to both axial and rotational motion when fitting 22' is used. This still allows the rod 26 to substantially maintain its position until moved or adjusted manipulated by a surgeon or other user. Thus the intermediate bend in the rod 26 can be equated with or considered to be another or alternate form of resistance mechanism which substantially maintains the position of the rod 26 until moved or adjusted by a surgeon or other user.

The second fitting 24 of FIGS. 1a and 1b is shown in greater detail in FIGS. 9a, 9b and 9c. The fitting 24 comprises a threaded portion 48 configured to engage thread T2, and an integral body portion 50. Body portion 50 is of a frusto-conical shape with a decreasing outer diameter in a taper direction D being away from threaded portion 48. A coarse screw thread 52 is formed about the conically shaped body portion 50. The crest of thread 52 has a flattened surface orientated so that a line 53 on the surface of the crest is inclined parallel with a central axis 55 of second portion 24. An axial through hole 57 is also formed through second portion 24. This allows for the passage of the inner manipulator rod 26 and/or other instruments as well as fluids including saline, dye, and air. In this embodiment of the manipulator 10, second fitting 24 is a cervical screw which is configured to screw into the cervix forming an attachment point as well as a seal.

However, alternate forms of second fittings may be incorporated in the manipulator 10. FIGS. 10a-10d illustrate an alternate second fitting 24a. Fitting 24a is in the form of a hollow probe having a threaded portion 48a and a body portion 50a. Threaded portion 48a has a thread configured to engage with thread T2. Body portion 50a is in the form of a tubular member which is open at its distal end 56 and is closed at an end 58 near threaded portion 48a to define or otherwise form a cavity 60. Distal end 56 is formed with a chamfer or bevel 62 to assist in insertion of the fitting 24a into a body cavity such as a vagina or rectum. Fitting 24a may be used for example during a hysterectomy to maintain pneumoperitoneum after removal of the uterus. The cavity 60 also allows for collection of pelvic tissue and specimens from the abdominal and pelvic cavities. A lumen (i.e. through hole) 64 may be formed axially through a circumferential wall 66 of the body 50a. In one embodiment the lumen 64 may have an internal diameter of approximately 6 mm to enable the receipt of a 4 mm telescope to enable illumination and visualization of tissue in cavities. For example this may be used in pelvic floor operations where the vagina and rectum septum need to be dissected out. This reduces the possibility of a recto-vaginal fistula occurring.

It is envisaged that the fitting 24a may be made in a variety of different sizes and in particular different diameters. For example 40 mm outer diameter, 30 mm outer diameter, and 20 mm outer diameter.

FIG. 11 illustrates one form of a forceps holder 70 that may be incorporated in an embodiment of manipulator 10. The forceps holder 70 is configured to seat on the elongated hollow tube 12 and releasably lock at a desired location along the tube 12. Forceps holder 70 comprises a first component 72 that is able to slide over and along tube 12 and is provided with detents 74 for gripping a handle of the forceps. Two detents 74 are shown on opposite sides of a central boss 76. However in other configurations alternate numbers of detent 74 may be provided. The boss 76 is provided with a screw thread 78 extending from a cross piece 80 which contains the detent 74. Extending axially from the thread portion 78 is a split collar 82. The forceps holder 70 also includes a locking nut 84 that is able to screw onto the threaded portion 78 over the split collar 82 and act to clamp the collar 82 onto an outer surface of the tube 12 thereby releasably locking the holder 70 at an outside location along the tube 12. In one example, the forceps holder 70 may be used to hold vulsellum forceps which in turn holds the manipulator 10 to the cervix making the manipulator self-retaining.

With reference to FIGS. 12-14b, the manipulator 10 may also support a cervical funnel 90 and a plug 92. The cervical funnel 90 is formed as a unitary device comprising a tube 94 of constant inner and outer diameter and an integral conical portion 96 which increases in outer diameter in a direction away from first end 16 of tube 12. The conical portion is provided with a lip 98 that extends about a part of the circumference of conical portion 96 and is flared in a radial outward direction.

Figure 12:
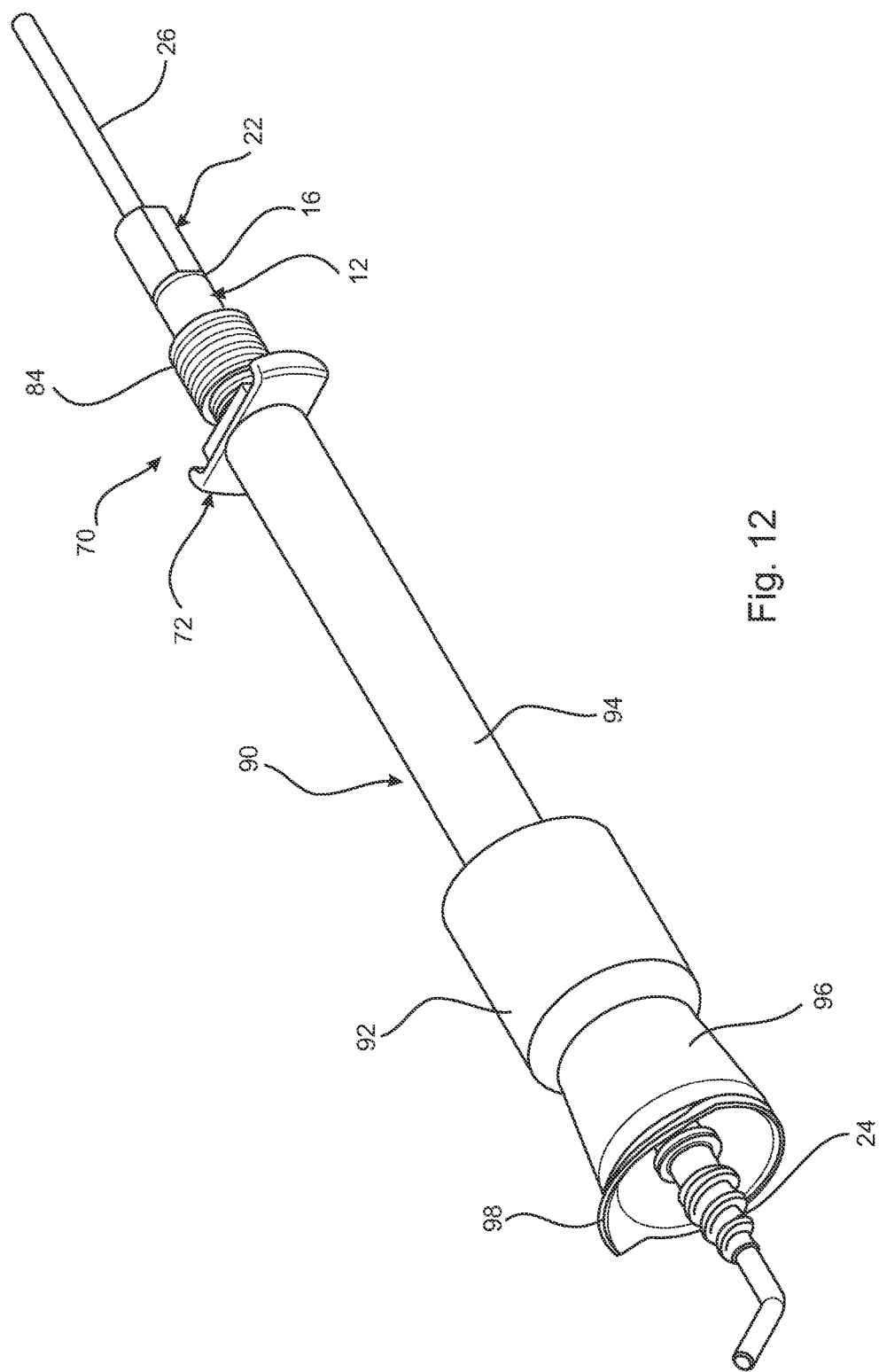
FIG. 12 is an isometric view of an embodiment of the general uterine manipulator and associated system with additional fittings to enable performance of a total laparoscopic hysterectomy; and, FIG. 13a is a side view of a cervical funnel incorporated in an embodiment of the general uterine manipulator shown in FIGS. 1a and 1b.

Plug 92 sits on the outside of funnel 90 and when used in gynaecological procedures forms a plug in the vagina. With reference to FIG. 12, it can be seen that the forceps holder 70 may also act as a positioning device for the funnel 90.

FIGS. 13a and 13b depict in greater detail the cervical funnel 90 incorporated in the manipulator 10 shown in FIG. 12. The lip 98 is flared outwardly by an angle θ of approximately 130° but may lay in the range of 130°-160°. In this embodiment the outermost edge of the lip 98 extends for an arc α of approximately 115° about the conical portion 96 but may lay in the range of about 100°-130°. An inside diameter of the tube 94 is arranged to be slightly greater than the outer diameter of the tube 12 to enable the cervical funnel 90 to be rotatably and linearly moveable with respect to the tube 12.

Figure 14B:
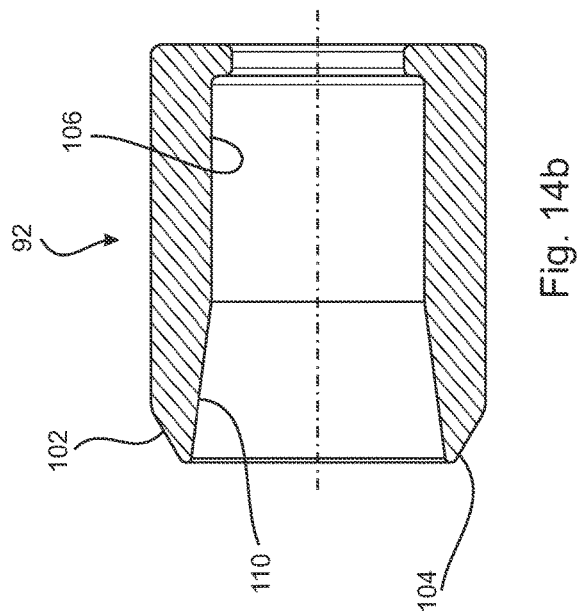
Figure 14A:
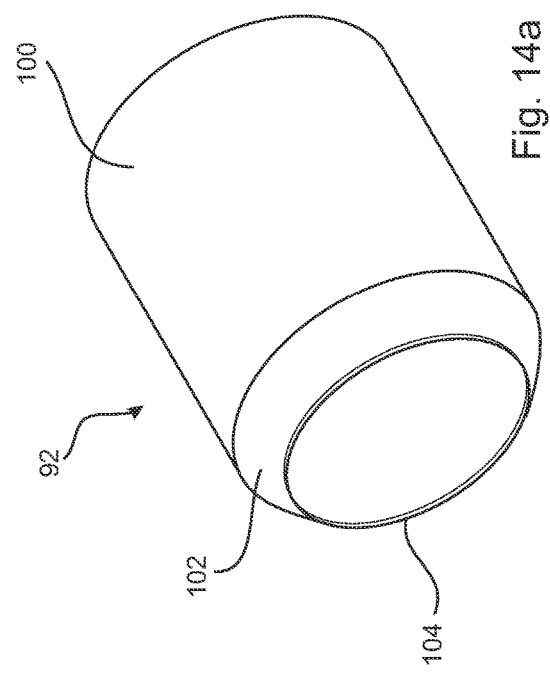
FIG. 14a is an isometric representation of a vaginal plug incorporated in an embodiment of the general uterine manipulator shown in FIGS. 1a and 1b.

FIGS. 14a and 14b depict in greater detail the vaginal plug 92 shown previously in FIG. 12. The plug 92 has a main body 100 formed of a constant outer diameter and a contiguous distal end portion 102 of progressively reducing outer diameter tapering to the distal end 104 of the plug 92. When the plug 92 is used with the manipulator 10, it is orientated so that the distal end portion 102 is directed toward the second fitting 24. An interior surface 106 of the plug 92 has a first portion 108 of constant inner diameter, and a contiguous second portion 110 of progressively increasing outer diameter. More particularly, the surface of the portion 110 is arranged to seat an exterior surface of the conical portion 96 of cervical funnel 90. Thus the increase in inner diameter of the surface of portion 110 is substantially the same as the angle of increasing diameter of the outer surface of conical portion 96.

Figure 15:
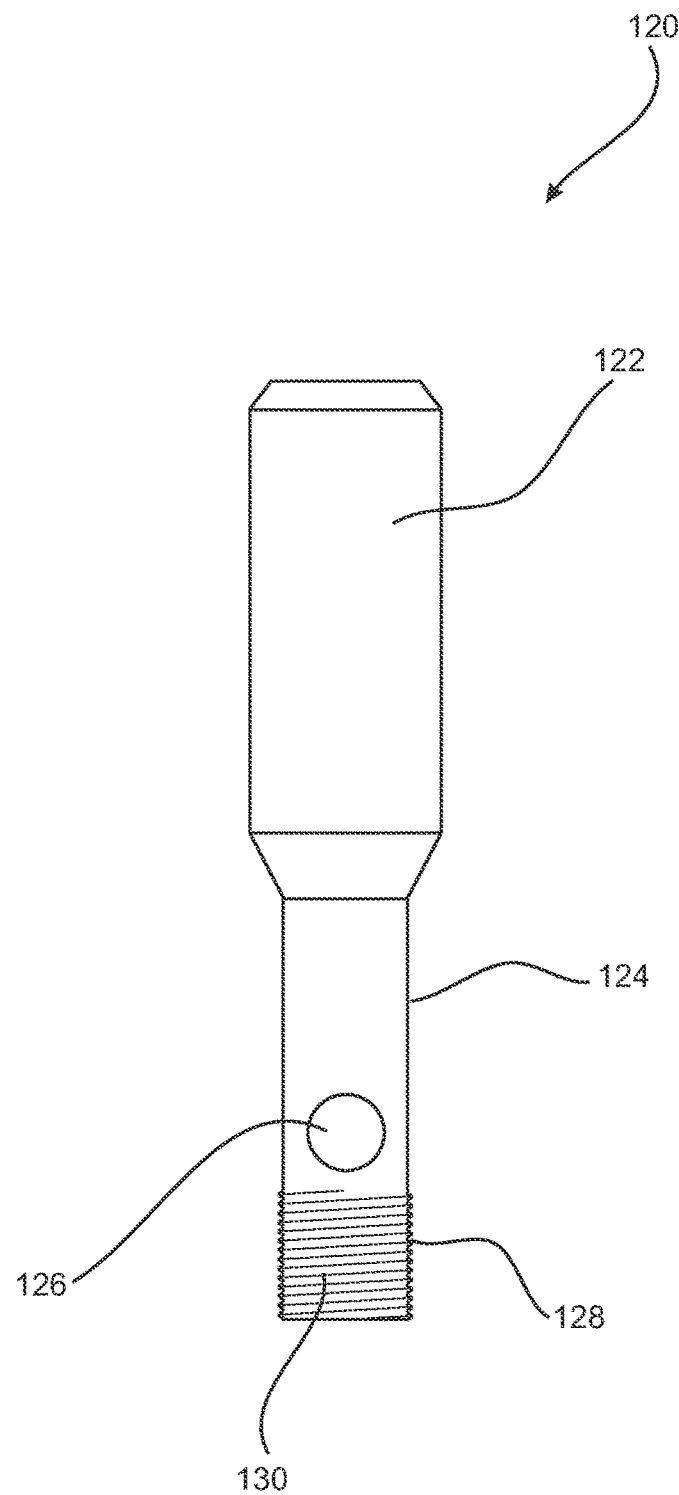
FIG. 15 is a side view of a manipulator handle which may be incorporated in an embodiment of the general uterine manipulator.

FIG. 15 depicts an optional handle 120 incorporated in embodiments of the manipulator 10. The handle 120 comprises a grip 122 and a contiguous extension 124. The extension 124 is provided with a through hole 126 and a screw thread 128. The screw thread 128 extends from approximately the location of the hole 126 to an end 130 of the handle 120. The through hole 126 is dimensioned to enable the tube 12 to pass there through either with a slight interference fit or a small clearance. Thus the handle 120 extends perpendicular to the tube 12. The screw thread 130 is configured to enable coupling with a nut such as a second locking nut 84. The locking nut when tightened on screw thread 128 can then act to clamp the handle 120 to the tube 12. The handle 120 can be applied to any portion of the tube 12 between the end fittings 22 and 24 which is not otherwise covered by other components such as the cervical funnel 90.

From the above description it will be recognised that dependent on the application at hand the manipulator may take many different forms owing the interchangability of first and second fittings and the ability to use additional components such as the rod 26, the forceps holder 70, cervical funnel 90 and the plug 92. It is envisaged that a general uterine manipulator system or kit may be provided to surgeons and doctors composed of all or at least a selection of the first and second fitting; together with other components such as the rod 26, forceps holder 70, cervical funnel 90 and the plug 92. In this way the surgeon or doctor will always have at hand various components to enable the performance of many different procedures.

FIGS. 16a-16d illustrate a further form of a second fitting 24b which primarily differs from the second fitting 24a by the inclusion of an illumination device 140. Features of the fitting 24b that have the same structure or function as the fitting 24a are designated with the same reference numbers. In this embodiment the illumination device 140 is in the form of a ring 142 fitted to or otherwise supported at the distal end 56 of fitting 24b. The illumination device 140 enables light to be emitted from the distal end 56. In one form the ring 140 is a ring of material embedded with one or more light emitting diodes (LEDs) 124. In this embodiment ring 142 may be made from a transparent acrylic resin. Power to the LEDs 144 is provided via a cable 146 that extends through the lumen 64. In the embodiment the lumen 64 may nevertheless be configured to also receive a telescope to enable visualization of the body cavity into which the fitting 24b is inserted. In a variation of the illumination device 140, the ring 142 itself comprises a light guide that receives light from an optical fiber that passes through the lumen 64. Light transmitted through the optical fiber enters and travels about the ring 142 thus enabling the emission of light from the distal end 56.

FIGS. 17a-17c depict a cervical funnel 90a which differs from the cervical funnel 90 by the provision of a light emitting device 140a enabling the emission of light form distal end 99 and more particularly from the 98 of the funnel 90a. The funnel 90a has essentially the same physical structure as a funnel 90 and accordingly includes a first conical portion 96 and integrally formed tube 94. The lip 98 extends partly about an opening 101 formed at the distal end 99. The illumination device 140a comprises an arcuate transparent body 142a which may for example be made from of a transparent acrylic resin. Coupled to the body 142a is an optical fiber 146 which is arranged to transmit light from a source to the body 142a. The body 142a has a configuration enabling it to be attached to the lip 98 in a manner so as to form a substantially continuous surface of the lip 98. The optical fiber 146 extends can through a channel or hole 148 formed in the funnel 90a. In one embodiment, a channel or groove can be cut in the exterior surface of the body 90a in which the optical fibre 146 is laid. Thereafter the groove can be filled with a resinous material and smoothed, effectively encapsulating the fiber 146 in the funnel 90a. A coupling 148 at the end of the optical fiber 146 enables coupling with a light source or another optical fiber which carries light from the light source. In a variation to the illumination device 140a, the body 142a may have embedded therein one or more LEDs which when provided with electric current either: emit light directly from the body 142a; or alternatively transmit light into the body 122a from which it is emitted. In the event that the body 122a carries one or more LEDs, then the optical fiber 126 is replaced with a wire or cable to provide electrical power to the LEDs.

FIG. 18 illustrates a manipulator 10 similar to that shown in FIG. 12 but with a modified cervical funnel 90b and a motor 150 arranged to rotate the cervical funnel 90b on, and relative to, the tube 12. The motor 150 is held within a housing 152 which is supported on a bracket 154. The bracket 154 is a squared U shaped configuration with opposed arms. The motor 150 is attached to one of the arms and a clamp 155 attached to the other arm. The clamp 155 can be operated to selectively grip and release the tube 12. When the clamp 155 is tightened it grips the tube 12 preventing axial or rotational motion of the tube 12.

The cervical funnel 90b is provided with a wave like outer surface profile on its tube 94 as depicted most clearly in FIG. 19. Successive troughs 156 and peaks 158 of the wave like profile act as rounded gear teeth about the periphery of tube 94b. These engage with a complementary shaped annular gear 160 driven by the motor 150. When the motor 150 is energized it rotates the gear wheel 160 and, due to its engagement with the outer surface of the tube 94b, causes the funnel 90b to rotate about and on the tube 12. Due to the manner of engagement of the motor 150 with the outer surface of the tube 94, the funnel 90b can be slid linearly along the tube 12 while maintaining engagement with the motor 150. The bracket 154 is attached to an arm 162 that in turn can be clamped on to a stable support such as an operating table. A foot controlled switch 164 communicates with the motor 150 via a cord 166. A surgeon is able to operate the motor 150 by the foot operated switch 164. The motor may be in the forms of a bi-directional stepper motor and the switch arranged to control the direction of rotation. The illuminating device 120a depicted in FIGS. 17a-17c may also be incorporated with the funnel 90b.

FIGS. 20a-20c illustrate variations of a medical instrument that may be used with the manipulator 10. In FIG. 20 the medical instrument 170 comprises in effect the second fitting 24a or 24b formed back to back and integrally with the cervical funnel 90 or 90a. The second fittings 24a, 24b differs slightly from those previously described in that they does not comprise a thread portion 48 but rather have a through hole at their proximal end 172 that communicates with the tube 94. Instrument 170 may be considered as comprising a body 174 provided with opposite first and second end portions 176 and 178. First end portion 176 has a first opening 180 and the second end portion 178 has a second opening 182. A throughway 184, constitute by the tube 94 extends between the first and second openings 180 and 182 and is arranged to enable the body 174 to be supported on a shaft such as the tube 12. With reference to FIG. 1a, if the end of the manipulator 10 provided with the cervical screw 24 is taken is the leading end, then the instrument 170 can be supported on the tube 12 with either of the first and second end portions 176, 178 at the leading end of the manipulator 10. Whichever of the end portions 176 or 178 is at the leading end will be inserted into the body cavity during a medical procedure.

In the embodiment in FIG. 20, it can be readily seen that the end portions 176 and 178 differ in one or more of their shape, size and configuration. In particular in FIG. 20, the end portions 176 and 178 differ in at least their shape and configuration. End portion 176 has an outer diameter D1 measured in a plane of the opening 180 while the end portion 178 has an outer diameter D2 measured in a plane containing opening 162. In this embodiment D1 may equal D2 or alternatively D1 and D2 may be different.

FIG. 21 illustrates an alternate form of medical instrument denoted as 170a comprising an opposite first and second end portions 176a and 178a respectively joined by an integral tube 94. Each of the portions 176a and 178a is of the general configuration of the portion 178 described in FIG. 20 but with different outer diameters D1 and D2. In particular in this embodiment D1 is less than D2. Instrument 170a would be used in substantially the same manner as the second fitting 24a or 24b. However having the two end portions of different diameters D1 and D2 allows a medical specialist to simply use the end of instrument 170a which is dimensioned for the best suit the body cavity into which it is to be inserted.

FIG. 22 illustrates a form of the medical instrument 170b in which the first and second end portions 176b and 178b are both of the same general frusto conical configuration as the first end portion 176 in FIG. 20. The difference between the end portion 176b and 178b being their respective outer diameters D1 and D2. In this specific embodiment D1 is greater than D2. When the instrument 170b is used with the manipulator 10 a medical specialist orientates the instrument 170b with the end portion 176b or 178b at the leading end determined on the basis of the best match of outer diameter D1 or D2 to the vagina in to which it is to be inserted.

The instruments 170-170b may be considered to be double ended instrument as each of the end portions 176-176b and 178-178 is configured to be inserted in a vagina or rectum. FIGS. 23a-23c illustrate a further form of double ended instrument 200 for insertion into a body cavity. Double ended instrument 200 comprises a body 202 having a first probe 204a and a second probe 204b (referred to in general as "probe(s) 204") at one end 206 and an opposite end 208 respectively of the body 200. The same reference numbers will be used to denote the same features of each probe. Reference number that includes the suffix "a" relate to the features of probe 204a; reference the number that includes the suffix "b" relate to the features of probe 204a; and reference numbers with no suffix "a" or "b" refer the feature in general pertaining to either probe 204a or 204b.

The first probe 204a has a cylindrical portion 210a of a first circumferential surface 212a having an outer diameter Da. Probe 204a is also provided with a first circumferential edge 214a at the first end 206 and a first lip 216a projecting outwardly from the outer circumferential surface 212a and beyond the first circumferential edge 214a. The first lip 216a extends for a part of the circumference of the edge 214a. The lip 216a may extend for between 100-130° of the circumference. This is akin to the angle α and the angular extent of the lip 98 shown in FIG. 13c.

The second probe 204b has the same general configuration as the probe 204a but with several differences including in dimensions of various aspects. The probe 204b has a cylindrical portion 210b with an outer circumferential surface 212b having an outer diameter Db. At the end 208 the probe 204b is formed with a second circumferential edge 214b and a second lip 216b. The second lip 216b projects outwardly from the outer circumferential surface 212b and beyond the second circumferential edge 214b.

In this embodiment the diameters Da and Db are different from each other. In particular Da is >Db. In one example the diameter Da is about 40 mm while the diameter Db is about 30 mm. A further difference in the dimensions and configuration of the probes 204a and 204b is that the lip 216b projects at a greater angle θ with respect to its corresponding adjacent second outer circumferential surface 212b. As a result the lip 216b is inclined at a shallower angle to a central longitudinal axis of the instrument 200 than lip 216a. In a general sense, each of the lips 216 projects at an angle θ relative to its adjacent circumferential surface 212 where θ is in the range of 130°-160°. This is akin to the angle θ of the lip 98 shown in FIG. 13b. However in this specific embodiment the angle of projection of the lip 216a is about 140° whereas the angle θb for the lip 216b is about 154°.

A further difference between the probes 204 is the axial difference by which each of the lips 216 project in the axial direction. The lip 216a which is inclined at a steeper angle than the lip 216b projects in an axial direction from a location immediately adjacent the outer circumferential surface 212a by a length La. The length La is different to and shorter than the length Lb of axial extent of the lip 216b. In one specific example, the distance La may be in the order of 9 mm where the distance Lb may be in the order of 13 mm.

Probe 214a is provided with an internal cavity 220a of circular cross section and having an inner diameter 222a. The outer circumferential edge 214a is formed by tapering or flaring the material of the probe 204a at the end 206. The angle of the taper is shown as angle β in FIG. 23b and may lie in a range of 110°-140°. However in this specific embodiment flaring angle β is 130°.

The internal configuration of the probe 204b is generally the same as that of probe 204a but with different dimensions. Specifically, the probe 204b has an internal cavity 220b with an internal diameter 222b which is not the same as and more particularly smaller than the internal diameter 222a. In one example the diameter 222a is about 35 mm and the diameter 222b is about 35 mm. The probe 204a at the end 208 is also tapered to reduce in thickness at an angle βb which is different to and in this embodiment less than the angle βb. In one example, the angle βb may be 116°.

The probe 200 is formed so that the lips 216 have respective circumferential mid points 224a and 224b that are in axial alignment. Thus when one probe 204 is inserted into a body cavity with the other probe outside of the cavity, a surgeon is able to easily visualize the position of the lip on the inserted probe by simple reference to the position of lip of the non-inserted probe. The arcuate extend of the lips 216, i.e. the angles αa and αb can be arranged to be the either the same or different. However in this specific embodiment the angle αa>αb.

The double ended probe 200 is also formed with an intermediate portion 226 that smoothly transitions between the probes 204a and 204b. The probe 226 has a central region 228 which is necked and has an outer diameter less than each of the diameters Da and Db. Thus, the outer circumferential surface 230 of the intermediate portion 226 has a concave profile. In one example the overall length of the probe 200 is about 230 mm with each probe 204 having a length of 85 mm and the intermediate portion having a length of 60 mm.

As shown most clearly in FIG. 23b, the intermediate portion 226 is formed with an internal bore 228 that extends in an axial direction between and providing fluid communication with the first and second cavities 220a and 220b. The bore 228 enables the double ended instrument 200 to be supported on the manipulator 10 and in particular the hollow tube 12 in the same manner as the funnel 90 and the medical instruments 170, 170a and 170b.

In a general sense, the double ended medical instrument 200 comprises a combination of the instrument 170a shown in FIG. 21 but with the addition of the funnel lips 98 and a reshaping and smoothing of the tube 98 and respective adjacent back ends of the portions 176a and 178a.

Figure 24D:
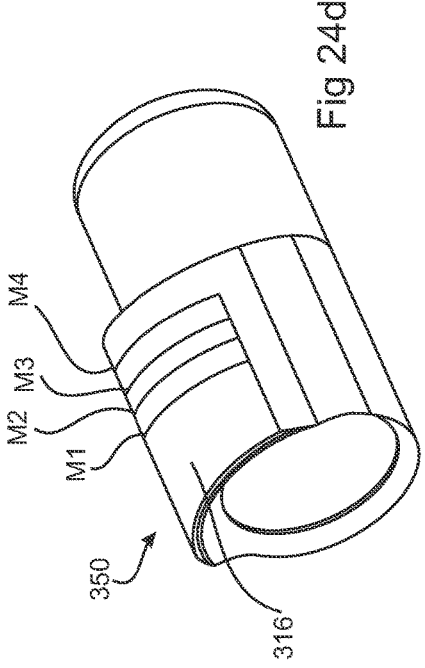

FIGS. 24a-24c depict a further embodiment of a double ended medical instrument. In this embodiment the double ended medical instrument is denoted by the reference number 300. The medical instrument 300 is a modified form of the medical instrument 200. All features of the medical instrument 300 that are the same as those of the medical instrument 200 are denoted with a reference number incremented by 100. For example, the probes of the medical instrument 300 are denoted by the numbers 304a and 304b, the lips are denoted by the reference numbers 316a and 316b and the intermediate portion is denoted by the reference number 326. Also as with the numbering convention for the instrument 200, reference number that includes the suffix "a" relate to the features of probe 304a; reference the number that includes the suffix "b" relate to the features of probe 304a; and reference numbers with no suffix "a" or "b" refer the feature in general pertaining to either probe 304a or 304b.

The double ended medical instrument 300 differs from the double ended medical instrument 200 solely by the provision of a platform 350a on the probe 304a; and a platform 350b on the probe 304b. Platform 350a has a constant first outer diameter extending over the cylindrical portion 310a. More particularly, the platform 350a has an outer circumferential surface 352a that is concentric with the outer circumferential surface 310a but of a greater radius. The platform 350a extends rearwardly from the outer circumferential edge 318a of the corresponding lip 314a. Also in this example the circumferential extent of the platform 350a is the same as that of the underlying lip 316a. The platform 350a extends in an axial direction toward the second probe 304b. Thereafter, the platform smoothly transitions from its rearward edge 354a to the circumferential surface 310a. This transition forms a ramp 356a between the outer circumferential surfaces 352a and 310a. Opposite sides 356a and 358a of the platform 350a transition smoothly to the outer circumferential surface 318a. Indeed rounded surfaces can be provided between the outer circumferential surfaces 352a and the sides 356a and 358a.

In this embodiment, the length Pa, that is the axial length of the platform 350a is in the order of 20 mm. While this distance may be varied and in particular extended the significance of the 20 mm length will be described in greater detail below. Suffice to say that it is possible to increase this length to say 30 or 40 mm and have tactile markers for example circumferential ridges or circumferential grooves at various set distances or lengths such as 20 mm, 25 mm, 30 mm, 35 mm.

The platform 350b is of the same general shape and configuration as the platform 350a. However the radius of the platform 350b is different to and in this embodiment smaller than the radius of a platform 350a. Further, as the lip 314b is formed with a smaller arc angle αb, the circumferential width of the platform 350b is smaller than that of platform 350a. However, the axial length Pb of the platform 350b in this embodiment is the same as the length Pa.

Each of the double ended medical instruments 200 and 300 may be used in laparoscopic gynecological surgery and in particular, for laparoscopic hysterectomy. The instrument 200 may be considered as a "standard" model and the instrument 300 as an "oncology" model.

Each of the medical instruments 200 and 300 can be slid over the uterine manipulator and in particular the tube 12 as described herein above in relation to the instruments 170, 170a and 170b. Alternatively, the medical instruments 200 and 300, and other medical instruments disclosed herein, can be inserted into a body cavity on their own without the uterine manipulator. In some embodiments, as further described below, a plug is inserted into the medical instrument to pneumatically plug the medical instrument when the medical instrument is inserted into a body cavity without the uterine manipulator. The specific probe which is inserted is simply dependent upon the size of the cavity at hand. An advantage or benefit of the instruments 200 and 300 over say the instrument 170b shown in FIG. 22 is that as the probe 204 or 304 is of a cylindrical shape rather than in the form of a frusto conical funnel, the outer surface 210 can act as a stopper in say the vaginal cavity to prevent leakage of $CO_2$ gas. Thus the probes 204 may be considered as integral functional combination of the instrument 170b shown in FIG. 22 together with respective plugs 92. In this way the instrument 200/300 can replace the instrument 170b and respective stops 92 for each of the portions 176b and 178b of the instrument 170b.

The lips 216/316 function as previously described to present the vaginal vault tissue for incision. After a hysterectomy is performed and the uterus is delivered through the vagina, usually an appropriate sized probe is inserted to prevent $CO_2$ leakage. This function is now performed as mentioned before by the provision of the cylindrical probes 204/304. A suture needle can be placed in the cavity 220/320 of the inserted probe 204 to be picked up by a laparoscopic needle holder to subsequently suture the vaginal vault.

The instrument 300 by virtue of the provision of the platforms 350 may be used in oncology procedures relating to cervical cancer. When cervical cancer is detected in the early stages, common procedure is to remove a 20 mm cuff from the vagina to adequately excise cancer tissue. Usually there is no indicator of how much margin to incise apart from the surgeon's subjective perception of adequate cuff removal. The instrument 300 provides a platform 350 of known length for example 20 mm to indicate to the surgeon the line of incision to remove an adequate margin of vaginal cuff. By rotating the lip 314 the vaginal margins are freed from the bladder anteriorly, the uterine vessels laterally and the rectum posteriorly, ensuring that these important structures are clear from the vaginal cuff before the vaginal incisions are made. The principles and functions of the instrument 300 is the same as the standard instrument 200 after the uterus and cervix is removed.

To the best of the Applicant's knowledge there is no vaginal marker colpotomizer available to accurately measure the vaginal margin of clearance that is required for gynecological oncology cases both in laparoscopy and open incision or laparotomy surgery. If too much vaginal tissue is removed the shortened vagina will make intercourse uncomfortable. Conversely, inadequate margins will result in cancer recurrences. Current practice is to gauge the depth of vaginal margin by estimation, and every surgeon has their own estimation method. Embodiments of the instrument 300 provide an accurate measuring tool for adequate vaginal margin removal to ensure the patient has the best clearance result and the best chance to have a functioning vagina. The platforms 350 provide a hard surface to push away the bladder anteriorly and the rectum posteriorly. The lips 314 ensure adequate ureteric displacement. The vagina is dissected at the edge of the platform 250. This can be performed in a number of different ways including but not limited to:

(a) a knife cutting along the end of the platform 350;
(b) cautery or cutting current being applied by a hook electrode or sharp scissors to the edge of the platform 350;
(c) harmonic scalpel energy to incise the vagina at the edge of the platform 350;
(d) a recessed trough at an edge of the platform 350 to guide vaginal incisions;
(e) by providing a hole near an edge of the platform 350 into which an electrode, monopolar or bipolar is inserted. In this event by rotating the instrument 300 the vagina is incised by the energy source being applied.

Figure 26:
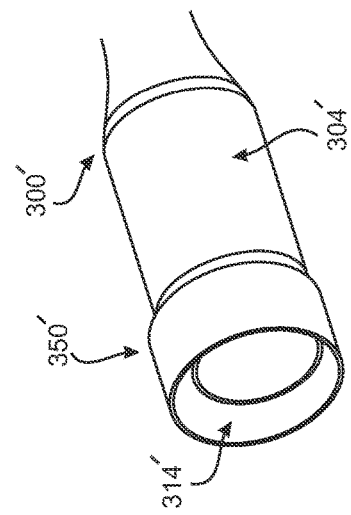
FIG. 26 illustrates one end of a modified form of the double ended medical instrument shown in FIG. 24a having a full circumference platform.

FIG. 26 depicts one end only of a further embodiment of a double ended medical instrument 300' which differs from the instrument 300 by virtue of its platforms 350' and the lips 314' that extend for the full circumference of the respective probe 304'. (The opposite end of the instrument 300' is of the same general configuration as shown in FIG. 26 but with the probe 304' at that end being of a different dimension akin to the differences between probes 204a and 204b; or 304a and 304b.) The instrument 300' can be used in laparotomy or open surgery. In these cases, the platform can be directly palpated hence there is no need to rotate the lip 314'/platform 350' to visualize the margin as in laparoscopic surgery. By a direct palpitation the vaginal margin is reflected before incisions are made to remove a desired length of vaginal cuff, for example 20 mm.

Figure 24E:
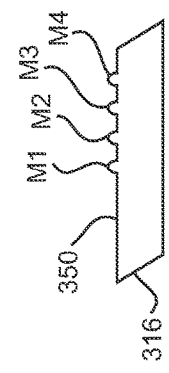
FIG. 24e depicts a cross section of a platform of the probe shown in FIG. 24a with markings in the form of ridges.
Figure 24F:
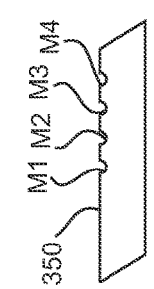
FIG. 24f depicts a cross section of a platform of the probe shown in FIG. 24a with markings in the form of grooves.
Figure 24G:
FIG. 24g depicts a cross section of a platform of the probe shown in FIG. 24a with markings in the form of sets of adjacent grooves and ridges.

As mentioned hereinbefore, the platform of the instrument 300 or 300' used in laparotomy or open surgery can be provided with an axial length P greater than say 20 mm with palpatible markings such as circumferential ridges or grooves at set lengths or distances to provide an indication of a precise length of vaginal cuff for incision. This is shown for example in FIGS. 24d-24g where markings M1-M4 are provided on the platform 350 at spacings of 20 mm, 25 mm, 30 mm, and 35 mm from the outer edge of associated lip 316. In FIG. 24e the markings M are ridges, in FIG. 24f the markings M are grooves, and in FIG. 24g the markings M comprise sets of immediately adjacent circumferential grooves and troughs. The double ended medical instrument with the platform and lip that extend wholly about the respective probes 304 may be termed as the laparotomy double ended instrument.

In the case of sacrocolpopexy where the bladder and rectum are reflected back to facilitate placement of mesh on the vagina, the platforms 350/350' in both the oncology and laparotomy double ended medical instrument provide a solid dissecting base. However in the event of use of the oncology double ended medical instrument 300 rotation may be required in order to place the platform 350 in the appropriate location. Clearly no rotation is required for the laparotomy double ended medical instrument 300'.

Figure 25:
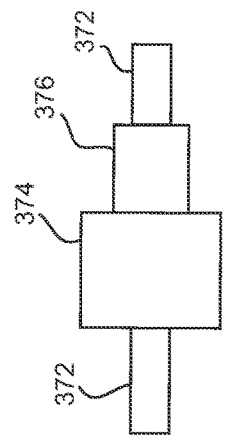
FIG. 25 illustrates a plug that can be used with the instruments depicted in FIGS. 20-24g.

A double ended plug 370 shown in FIG. 25 can be used with the either of the standard, oncology or laparotomy double ended medical instrument. The plug has an axially aligned and opposite cylindrical stems 372 of a diameter that provides a light interference fit with the inner circumferential surface at one end of the bore 228,328 of the intermediate portions. Between the stems 372 is a large diameter cylindrical portion 374 and an intermediate diameter cylindrical portion 376. The portion 374 is dimensioned to form a light interference fit with the cavity 220a, or 320a; and portion 376 is dimensioned to form a light interference fit with the cavity 220b, 320b of the probes 204b or 304b. The plug when fitted into the corresponding end of the medical instrument forms a fluid seal at that end of the seal. Naturally the plug 370 can only be used when the double ended instrument is not supported on the manipulator 10. It is envisaged that the plug 300 would be used to assist in maintaining pneumoperitoneum when the double ended instrument is used without the manipulator 10. In exactly the same way the plug 370 can be used with any one of the instruments, 170, 170a and 170b shown in FIGS. 20-22.

In some embodiments, a medical instrument, such as, for example, the various double ended medical instruments and cervical funnels described herein, is configured to maintain pneumoperitoneum without requiring a plug. For example, the medical instruments shown in FIGS. 20-22 may comprise a solid central section instead of a tube 94 with a throughway 184. In such an embodiment, the first opening 180 and second opening 182 are not in fluid communication with each other through the central section and therefore no plug is required. Further, in such an embodiment, there is no throughway 184, so a tube 12 cannot pass through the medical instrument. This may be advantageous for users that do not desire or require, for example, uterine manipulation, such as with some laparoscopy or laparotomy.

FIGS. 27a-27d illustrate further variations to the cervical funnel 90c. The funnel 90c is of the same general shape and configuration and works in the same way as funnel 90, but differs by the provision of a through hole 190 in the lip 98. The through hole 190 is provided mid way along the arc of the lip 98. Optionally the funnel 98 may also comprise an illumination device 192. In this embodiment the illumination device 192 is in the form of an annular light guide coupled to an optical fiber. The annular light guide 192 surrounds the through hole 190. When the optical fiber is coupled to a light source the light is guided by the fiber 194 to the annular light guide and illuminates the annular light guide 192 providing a ring of light about the hole 190. The annular light guide 192 can be in the form a transparent acrylic resin ring. The optical fiber 194 can be embedded/encapsulated in a groove formed along the cervical funnel 90d.

The hole 190 is dimensioned to receive the tip of an electrical cautery probe. During say a hysterectomy the probe is inserted into the hole 190. It is believed that the hole 190 will ordinarily be easily visible or locatable by a surgeon. However the provision of the illumination device 192 will assist in visually locating the hole 190. The electrical cautery probe is inserted through the vagina wall (which is being lifted by the lip 98) and into the hole 190. By applying electric current and rotating the funnel 90d a very clean and precise circumcision can be made of the vaginal wall to separate it from the cervix.

The through hole 190 may also of course be incorporated in every other form of cervical funnel described hereinbefore. As can the annular light guide 192.

FIGS. 28A-28C illustrate a further embodiment of a double ended instrument 2800. The double ended instrument 2800 is similar in design to the double ended instruments 200 and 300 illustrated in FIGS. 23A-23C and 24A-24C, respectively. The double ended instrument 2800 comprises a first probe 2804a, a second probe 2804b, and an intermediate portion 2826 positioned between the first and second probes. Unlike the double ended instrument 300, which comprises a generally concave intermediate portion positioned between that double ended instrument's first probe and second probe, the double ended instrument 2800 utilizes a generally cylindrical central region 2828 with generally tapered transition regions 2829a and 2829b positioned at either end.

As with other embodiments of double ended instruments, the first probe 2804a and second probe 2804b comprise cylindrical portions 2810a and 2810b which may be utilized, for example, as a plug to maintain pneumoperitoneum. The transition regions 2829a and 2829b can be configured to have a generally tapered shape to transition between an outer diameter of the central region 2828 and an outer diameter of each probe to, for example, enable smooth insertion into and retraction from a body cavity.

The double ended instrument 2800 further comprises a first lip 2816a and a second lip 2816b configured to operate similarly to the lips 216a and 216b of the double ended instrument 200. Namely, the first lip 2816a and second lip 2816b can be configured to, for example, present the vaginal vault tissue for incision. The double ended instrument 2800 further comprises a first marker lip 2817a and a second marker lip 2817b positioned a longitudinal distance 2850a and 2850b, respectively, from the first and second lips. In this embodiment, the distances 2850a and 2850b are each approximately 20 millimeters. The first and second marker lips can be utilized to, for example, act as visual landmarks to indicate where a surgeon should cut. For example, the double ended instrument 2800 may be utilized in oncology procedures, similar to as described above, to enable a surgeon to easily determine where to cut to remove the cuff from the vagina to adequately excise cancer tissue.

Although in this embodiment, the marker lips 2817a and 2817b are positioned approximately 20 millimeters in an axial or longitudinal direction away from the first and second lips, in various other embodiments, the marker lips can be positioned different distances away from the first and second lips to accommodate different lengths or margins of vaginal cuff to excise. In some embodiments, more than one marker lip is positioned on each of the probes. For example, multiple marker lips may be positioned at various distances from the first or second lip, similar to the indicators illustrated in FIGS. 24D through 24G. Further, in this embodiment, the outer edges of the first marker lip 2817a, first lip 2816a, second marker lip 2817b, and second lip 2816b comprise approximately the same included angle 2860. However, in other embodiments, the outer edges of the marker lips may comprise a smaller or a larger included angle than the first or second lips. Further, although the marker lips in this embodiment are illustrated as being rotationally aligned with the first and second lips along a central axis of the double ended instrument 2800, in other embodiments, the marker lips may be positioned at a different rotational orientation relative to the first and second lips and/or each other.

The double ended instrument 2800 further comprises a first cavity 2820a, a second cavity 2820b, and an internal bore 2829. The first and second cavities and internal bore can be configured to operate similarly to the internal cavities and bores of the double ended instruments 200 and 300 as further described above.

Pneumatic Plug

Figure 29B:
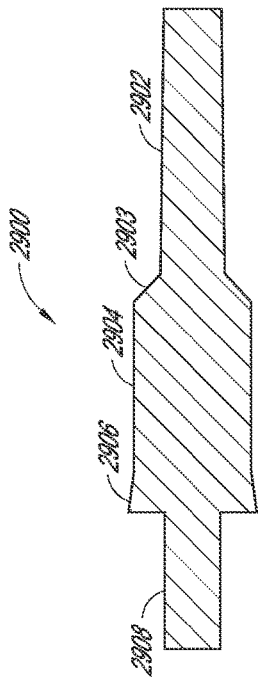
FIG. 29B illustrates a side cross sectional view of the pneumatic plug of FIG. 29A.
Figure 29C:
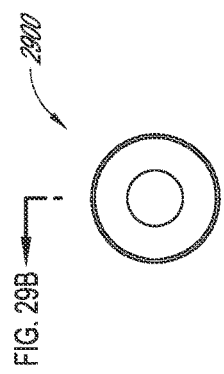
FIG. 29C illustrates a front view of the pneumatic plug of FIG. 29A.
Figure 29A:
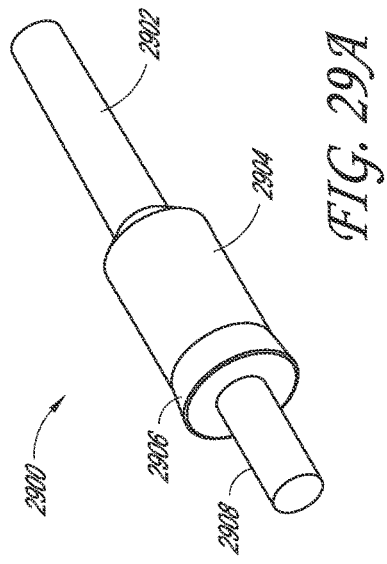
FIG. 29A illustrates a perspective view of an embodiment of a pneumatic plug.

FIGS. 29A-29C illustrate an embodiment of a plug 2900. The plug 2900 can be configured to operate similarly to the plug illustrated in FIG. 25, in that the plug 2900 can be configured to pneumatically plug, for example, a double ended instrument, such as the double ended instruments illustrated in FIGS. 28A-28C, 24A-24C, and 23A-23C. Note that, while the plug 2900 is described in this disclosure in relation to double ended instruments, such a plug may further be used with various other embodiments of cervical funnels, colpotomizers, and/or the like.

The plug 2900 comprises a first stem 2908, a second stem 2902, a central region 2904, and a tapered region 2906. The second stem 2902, in some embodiments, is configured to be inserted into an internal bore of a double ended instrument to plug the internal bore to maintain pneumoperitoneum. The plug 2900 would take the place of, for example, a hollow tube 12 as further described above. In this embodiment, the second stem 2902 is configured to be generally tapered to ease installation into and retraction from an internal bore, such as the internal bore 2829 illustrated in FIG. 28B. In this embodiment, the second stem 2902 comprises an approximately 12 millimeter outer diameter at a distal end and tapers to an approximately 13.8 millimeter outer diameter at a proximal end where the second stem 2902 meets the central region 2904. In some embodiments, as illustrated in FIG. 29B, the plug comprises a tapered region 2903 between the second stem 2902 and central region 2904. In some embodiments, the internal bore 2829 of the double ended instrument 2800 comprises an inner diameter of approximately 13.1 millimeters. Accordingly, the tapered second stem 2902 can be easily guided into the internal bore 2829 to generate an interference fit with the internal bore 2829 to enable an airtight or substantially airtight seal.

In some embodiments, the central region 2904 and/or the tapered region 2906 can be configured to generate an interference fit with one or more cavities of a double ended instrument to generate an airtight or substantially airtight seal. For example, in some embodiments, the second cavity 2820b illustrated in FIG. 28B comprises an approximately 25 millimeter inner diameter. Further, the central region 2904 of the plug 2900, in some embodiments, comprises an outer diameter of approximately 25 millimeters to enable an interference fit with the second cavity 2820b. In some embodiments, both the second stem 2902 and central region 2904 are configured to generate interference fits with a double ended instrument. In other embodiments, only one or the other is configured to generate an interference fit with a double ended instrument.

In some embodiments, the first stem 2908 can also be configured to generate an interference fit with, for example, an internal bore of a double ended instrument. In other embodiments, the first stem 2908 can be configured to operate merely as a handle to ease insertion and retraction of the plug 2900. In some embodiments, the tapered region 2906 can also or alternatively be configured to form an interference fit with an internal bore or cavity of a double ended instrument.

Pig Colpotomizer

FIGS. 30A-30C illustrate a double ended medical instrument or pig colpotomizer 3000. The double ended medical instrument 3000 has some features in common with the various medical instruments described above for use in, for example, laparoscopic hysterectomies. However, the double ended instrument 3000 is configured to be used with a pig, rather than a human.

When surgeons are training for laparoscopic surgery, the surgeons often use an animal model to teach laparoscopic techniques which involve incisions, dissections, energy use, and suturing. Various organs in an animal model are deliberately incised or removed to simulate events in the human patient. In the case of laparoscopic abdominal or vaginal surgery, piglets are typically weaned at four weeks old and then fed for another two weeks so that they weigh approximately 30 kilograms. Their abdominal cavities then sufficiently simulate a human and are suitable to be used for laparoscopic surgery training. The piglets' reproductive organs, however, especially the vagina, are typically not fully developed in size at this point. This is because female pigs typically breed at nine months, when they are sexually mature and weight approximately 120 kilograms.

Performing a total laparoscopic hysterectomy (TLH) using pigs is challenging anatomically due to, among other things, differing anatomy of the reproductive organs and small organ size, especially with the vagina, due to the relatively young age of the animals used. Accordingly, performing a successful TLH on a piglet has historically been a difficult task.

The pig colpotomizer or double ended instrument 3000 illustrated in FIGS. 30A-30C is configured to enable a surgeon to successfully perform a TLH on a young pig. A typical piglet's vagina is approximately 100 millimeters to 140 millimeters long. At the end of the vagina, an inner sleeve of cervix is attached. The cervix is connected to a short central body from which two uterine horns arise. In these horns, future piglets develop. At the end of each uterine horn there is an ovary and fallopian tube. Past hysterectomy workshops on a pig have involved resection of the central cervical body where the two uterine horns meet, not the vaginal-cervical junction as in a true TLH. Additionally, resection at the vaginal-cervical junction involves securing the uterine vessels either by energy or ligating, a step that most closely simulates TLH in the human. The technique of vaginal-cervical resection is not possible without a colpotomizer, such as, for example, the double ended medical instrument 3000, to accurately outline and delineate this anatomical landmark.

The double ended instrument 3000 comprises a colpotomizer portion 3004 and a dilator portion 3002. The instrument 3000 comprises generally an elongated cylindrical tool having the dilator portion 3002 on approximately one-half of the device and the colpotomizer portion 3004 on the other half. In some embodiments, an overall length of the instrument 3000 is approximately 250 millimeters. However, in other embodiments, the overall length and the length of each portion can vary.

The dilator portion 3002 is configured to gently dilate a pig's vagina by utilizing multiple graduated regions 3008. The dilator portion 3002 begins with a first end 3007 having a first outer diameter. The multiple graduated regions 3008 increase in diameter until the dilator portion 3002 meets the colpotomizer portion 3004, which has a cylindrical portion 3010 of a larger diameter than the nearest graduated region 3008 of the dilator portion 3002. In some embodiments, the graduated dilator commences at six millimeters outer diameter and increases to ten millimeters outer diameter in one millimeter increments. For example, the first end 3007 may be approximately six millimeters in outer diameter, while the cylindrical portion 3010 is approximately ten millimeters in outer diameter, with each graduated region 3008 comprising a diameter between six and ten millimeters.

In some embodiments, the cylindrical portion 3010 comprises an overall length of approximately 120 to 140 millimeters. The cylindrical portion 3010 comprises at one end an asymmetrical funnel or lip 3016. The lip 3016 can be configured to operate similarly to the lips illustrated in various other embodiments as described herein. The included angle 3060 of the lip 3016 can vary, as with other embodiments.

In use, the double ended instrument 3000 is operated by first inserting the dilator portion 3002 into the pig's vagina to dilate the vagina. Then, the double ended instrument 3000 is extracted, and the colpotomizer portion or asymmetrical funnel end is inserted and advanced to the end of the cervical canal. Similar to with the other cervical/vaginal funnels as further described above, when the colpotomizer is rotated, the asymmetrical end with the raised lip 3016 is configured to raise the vaginal vault (the junction between the cervix and the vagina) to, for example, indicate placement of the vaginal incision to the surgeon. After incision of the vagina to free the cervix, the cervix, uterus, ovaries, and tubes, which have been dissected prior to the vaginal incision technique, can be placed into the vaginal canal by gently pulling out the colpotomizer 3000. After extraction of the tissue, the colpotomizer 3000 can be inserted back into the vagina to prevent $CO_2$ leakage while the vaginal vault opening is closed by sutures. For example, the cylindrical portion 3010 can be configured to form an airtight or substantially airtight seal with the vaginal tissue.

In this embodiment, the colpotomizer 3000 is a solid device, unlike the hollow embodiments further described above as used with humans. One reason for this is that, in human operations, uterine manipulation is often required. However, in pig hysterectomy operations, uterine manipulation is often not required.

In some embodiments, the pig colpotomizer 3000 can be held in place in the pig's vagina by a person. In other embodiments, a medical instrument support is utilized to hold the medical instrument in position in the pig's vagina. For example, embodiments of such medical instrument supports can be seen in FIGS. 31A-31B, 32A-32B, and 33A-33B. FIGS. 31A and 31B illustrate an embodiment of a medical instrument support 3100. The medical instrument support 3100 comprises a generally circular disc having an outer diameter 3102 of approximately 60 millimeters to 80 millimeters, and a width 3104 of approximately ten millimeters. Note that, although the medical instrument support 3100 and other medical instrument supports described in this disclosure generally comprise a circular disc shape, various other shapes and sizes may be utilized as long as the medical instrument support adequately performs the functions as described herein with respect to supporting, for example, a pig colpotomizer.

The medical instrument support 3100 comprises a medical instrument port 3106 and an appendage port 3108. The medical instrument port 3106 can be configured to enable insertion of a medical instrument therethrough, for example, the pig colpotomizer 3000 illustrated in FIGS. 30A-30C, to enable support of the medical instrument and/or rotation of the medical instrument while inserted into the pig's vagina. In some embodiments, the medical instrument port 3106 can comprise an inner diameter of approximately 15 millimeters to 20 millimeters.

The appendage port 3108 can be configured to enable an appendage of a subject being operated on to be passed therethrough to anchor the medical instrument support 3100. For example, in this embodiment, the appendage port 3108 is configured to enable a surgeon to pass a pig's tail therethrough to anchor the medical instrument support 3100. In some embodiments, the tail is secured to the medical instrument support 3100 by placing a suture through the tail and passing the tail through the appendage port 3108, and optionally repeating that procedure one or more times until the tail is anchored securely. When an appendage is anchored to the medical instrument support 3100, this enables stabilization of the colpotomizer, while still allowing rotation of the colpotomizer within the medical instrument port 3106.

FIGS. 32A-32B and FIGS. 33A-33B illustrate further embodiments of medical instrument supports. The medical instrument support 3200 illustrated in FIGS. 32A and 32B is configured to operate similarly to the medical instrument support 3100, except the medical instrument support 3200 further comprises a sleeve 3210. The sleeve 3210 comprises a generally cylindrical tube extending from a face of the medical instrument support 3200 generally parallel to a central axis of the medical instrument port 3106. The sleeve 3210 can be configured to provide additional surface area for the support and stabilization of a medical instrument passing therethrough.

FIGS. 33A and 33B illustrate a further embodiment of a medical instrument support 3300. The medical instrument support 3300 is configured to operate similarly to the medical instrument support 3200. However, the medical instrument support 3300 utilizes a medical instrument port 3306 comprising a blind hole within the sleeve 3310, rather than being a through hole as with the embodiments illustrated in FIGS. 31A-31B and 32A-32B. In this embodiment, the medical instrument port 3306 is still configured to support a medical instrument, such as a pig colpotomizer, except the medical instrument can only be inserted up to the depth of the blind hole comprising the medical instrument port 3306.

Cervical Dilator

Figure 34:
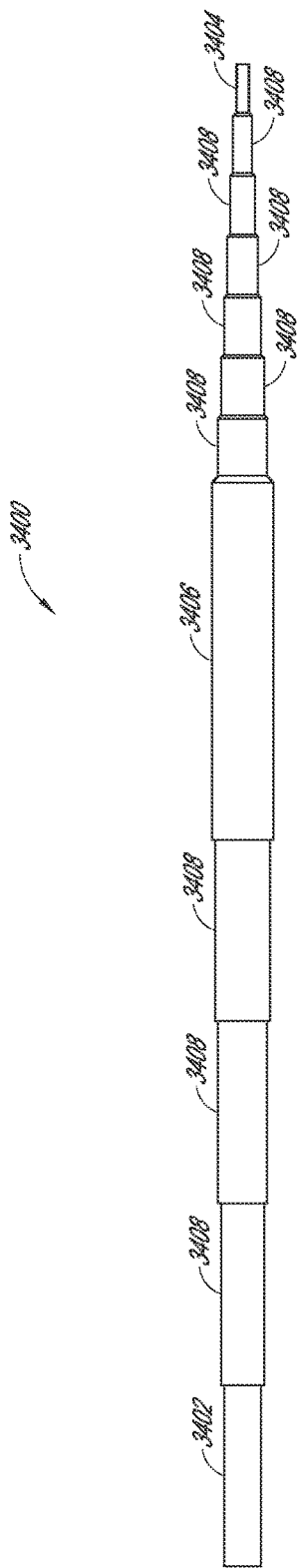
FIG. 34 illustrates a side view of an embodiment of a cervical dilator.

FIG. 34 illustrates a cervical dilator 3400 that can be utilized to dilate, for example, a human cervical canal. The cervical dilator 3400 comprises a first end 3402, a second end 3404, a central region 3406, and a plurality of graduated regions 3408 positioned between the first end 3402, the central region 3406, and the second end 3404. The cervical dilator 3400 can be configured to utilize the concepts illustrated by the dilator portion 3002 of the pig colpotomizer 3000 illustrated in FIGS. 30A-30C. Namely, the cervical dilator 3400 can be configured to gradually dilate a human or other animal cervical canal to enable the insertion of instruments to, for example, sample the uterus or to enable insertion of a hysteroscope to visualize the uterus. A typical uterine cavity length is approximately 70 millimeters to 80 millimeters. Accordingly, the overall length of the dilator 3400 and/or the length of each of its segments can be configured to accommodate various uterine lengths.

In use, the cervical dilator 3400 can be inserted into the vaginal canal, with the second end 3404 leading the dilator into the canal. The cervical canal can then be dilated gradually by further inserting the cervical dilator 3400 to enable the graduated regions 3408 of increasing diameter to gradually increase the dilation of the cervical canal. In some embodiments, only one end or half of the cervical dilator 3400 is utilized. For example, either the second end 3404 or the first end 3402 is inserted into the vaginal canal. Which end is inserted into the vaginal canal may depend upon, for example, the undilated diameter of the cervical canal. In some embodiments, both ends or halves are used to dilate a cervical canal. For example, the second end 3404 and its adjacent graduated regions 3408 can be inserted into the cervical canal to begin the dilation. Then, the cervical dilator 3400 can be extracted and flipped, and the first end 3402, along with its adjacent graduated regions 3408, can be inserted to complete the dilation up to potentially the largest diameter of the cervical dilator 3400, shown here in the central region 3406.

In some embodiments, one end or both ends of a cervical dilator can commence at two or three millimeters in diameter and gradually increase, at longitudinal distances from five millimeters to 20 millimeters, to outer diameters of any dimension within the limits of the overall outer diameter of the dilator. In some embodiments, one end of the dilator commences at the largest outer diameter of the opposite end. For example, referring to the cervical dilator 3400, in some embodiments, the first end 3402 may be configured to be approximately the same outer diameter as the largest graduated region 3408 of the opposite end of the cervical dilator 3400.

Cervical dilators as described herein can be advantageous for use in gynecological procedures. Such a one piece dilator can be easier to use than other potential solutions, such as dilators that comprise individual dilator rods each having a fixed outer diameter. Such rods may, for example, begin at two millimeters and progress to 20 millimeters or any other desired outer diameter, with a different rod being used for each diameter. If such dilator rods are used, a surgeon must insert and remove a plurality of dilator rods before the surgeon is able to get the cervical canal to the proper dilation. However, utilizing a cervical dilator such as the cervical dilator 3400 described herein, a surgeon can use a single tool to easily and quickly dilate the cervix. Further, a cervical dilator as described herein can more gradually dilate the cervix by incorporating a plurality of graduated regions 3408. When using dilator rods having fixed outer diameters, a surgeon may be tempted to use a smaller number of rods, and will not as gradually dilate the cervical canal. Accordingly, it can be seen that a cervical dilator such as the cervical dilator 3400 shown in FIG. 34 has several advantages over dilator rods of fixed outer diameter.

Now that an embodiment of the invention has been described in detail it will be apparent to those skilled in the relevant arts that numerous modifications and variations may be made without departing from the basic inventive concepts. For example, in one embodiment, the hydrotubation port 42 is illustrated and described as being formed on the first fitting 22. However in an alternate embodiment, a hydrotubation port may be formed on the tube 12 at a location near first end 16 but beyond the screw thread T1. In one embodiment, the first and second fittings 22, 24 may be formed from a plastics material so as to be disposable after a single use while the elongated hollow tube 12 may be made from surgical grade stainless steel so as to be reusable. Also as would be readily apparent to one of ordinary skill further double ended instruments may be constructed using combinations end portions or probes shown in FIGS. 20-26 of the same or different size. For example a double ended instrument could comprise: a probe 204a at one end and a probe 304a at another, where the probes are of the same or different outer diameter; a probe 204a at one end and a probe 304'a at another, where the probes are of the same or different outer diameter; an end portion 176a at one end and a probe 204b at the other, where the probes are of the same or different outer diameter; etc. All other combinations of the currently disclosed probes and end portions are possible. All such modifications and variations together with others that would be obvious to persons of ordinary skill in the art are deemed to be within the scope of the present invention the nature of which is to be determined from the above description and the appended claims.

What is claimed is:

1. A medical instrument for performing a laparoscopic oncology procedure, the medical instrument comprising:
   a probe comprising:
   an outer circumferential surface, the outer circumferential surface extending in a longitudinal direction and sized for non-traumatic insertion into a human vaginal cavity, wherein the outer circumferential surface is substantially cylindrical; and a lip projecting outwardly from the outer circumferential surface and extending circumferentially about only a portion of the outer circumferential surface, the lip configured to raise vaginal tissue to provide a visual landmark for dissection during the laparoscopic oncology procedure, the lip positioned such that the lip is set back from a distal-most point of the probe by approximately 20 millimeters and the outer circumferential surface extends both distally and proximally to the lip, wherein the outer circumferential surface comprises a surgical grade material comprising sufficient stiffness to support the lip in raising the vaginal tissue to provide the visual landmark for dissection during the laparoscopic oncology procedure, and wherein the probe comprises a hollow inner cavity; and a pneumatic plug configured to pneumatically plug at least a portion of the probe.

2. The medical instrument of claim 1, wherein the lip extends circumferentially about the outer circumferential surface through an arc that subtends an angle of at least 100 degrees.

3. The medical instrument of claim 1, wherein the probe further comprises:
a passage configured to enable a medical device to pass therethrough; and
the medical device, wherein the medical device comprises a uterine manipulator.

4. The medical instrument of claim 1, further comprising:
an elongate hollow body comprising surgical grade material, the elongate hollow body extending in a longitudinal direction from a proximal end to a distal end;
wherein the probe is disposed at the distal end of the elongate hollow body.

5. The medical instrument of claim 1, further comprising:
a second lip projecting outwardly from the outer circumferential surface and extending circumferentially about only a portion of the outer circumferential surface, the second lip configured to raise vaginal tissue to provide a visual landmark for dissection, the second lip positioned such that at least a portion of the second lip extends distally beyond a distal end of the outer circumferential surface.

6. A medical instrument for performing a laparoscopic oncology procedure, the medical instrument comprising:
a probe comprising:
an outer circumferential surface, the outer circumferential surface extending in a longitudinal direction and sized for non-traumatic insertion into a human vaginal cavity, wherein the outer circumferential surface is substantially cylindrical; and
a lip projecting outwardly from the outer circumferential surface and extending circumferentially about only a portion of the outer circumferential surface, the lip configured to raise vaginal tissue to provide a visual landmark for dissection during the laparoscopic oncology procedure, the lip positioned such that the lip is set back from a distal-most point of the probe by approximately 20 millimeters and the outer circumferential surface extends both distally and proximally to the lip, and
a second lip projecting outwardly from the outer circumferential surface and extending circumferentially about only a portion of the outer circumferential surface, the second lip configured to raise vaginal tissue to provide a visual landmark for dissection, the second lip positioned such that at least a portion of the second lip extends distally beyond a distal end of the outer circumferential surface;

wherein the outer circumferential surface comprises a surgical grade material comprising sufficient stiffness to support the lip in raising the vaginal tissue to provide the visual landmark for dissection during the laparoscopic oncology procedure, and wherein the probe comprises a hollow inner cavity;

an elongate hollow body comprising surgical grade material, the elongate hollow body extending in a longitudinal direction from a proximal end to a distal end, wherein the probe is disposed at the distal end of the elongate hollow body, and wherein the elongate hollow body transitions smoothly into the outer circumferential surface of the probe;

a second probe disposed at the proximal end of the elongate hollow body, the second probe comprising a second outer circumferential surface comprising a different diameter than the outer circumferential surface of the probe disposed at the distal end of the elongate hollow body; and a third lip projecting outwardly from the second outer circumferential surface and extending circumferentially about only a portion of the second outer circumferential surface, the third lip configured to raise vaginal tissue to provide a visual landmark for dissection during the laparoscopic oncology procedure.

7. The medical instrument of claim 6, wherein the lip extends circumferentially about the outer circumferential surface through an arc that subtends an angle of at least 100 degrees.

8. The medical instrument of claim 6, wherein the probe further comprises:
a passage configured to enable a medical device to pass therethrough; and
the medical device, wherein the medical device comprises a uterine manipulator.

9. The medical instrument of claim 6, wherein the second lip comprises the distal-most point of the probe.

10. A medical instrument for performing a laparoscopic oncology procedure, the medical instrument comprising:
a probe comprising:
an outer circumferential surface, the outer circumferential surface extending in a longitudinal direction and sized for non-traumatic insertion into a human vaginal cavity, wherein the outer circumferential surface is substantially cylindrical; and
a lip projecting outwardly from the outer circumferential surface and extending circumferentially about only a portion of the outer circumferential surface, the lip configured to raise vaginal tissue to provide a visual landmark for dissection during the laparoscopic oncology procedure, the lip positioned such that the lip is set back from a distal-most point of the probe by approximately 20 millimeters and the outer circumferential surface extends both distally and proximally to the lip;

wherein the outer circumferential surface comprises a surgical grade material comprising sufficient stiffness to support the lip in raising the vaginal tissue to provide the visual landmark for dissection during the laparoscopic oncology procedure, and wherein the probe comprises a hollow inner cavity; and a second lip projecting outwardly from the outer circumferential surface and extending circumferentially about only a portion of the outer circumferential surface, the second lip configured to raise vaginal tissue to provide a visual landmark for dissection, the second lip positioned such that at least a portion of the second lip extends distally beyond a distal end of the outer circumferential surface.

11. The medical instrument of claim 10, wherein the second lip comprises the distal-most point of the probe.

12. The medical instrument of claim 10, wherein the lip extends circumferentially about the outer circumferential surface through an arc that subtends an angle of at least 100 degrees.

13. The medical instrument of claim 10, wherein the probe further comprises:
  a passage configured to enable a medical device to pass therethrough; and
  the medical device, wherein the medical device comprises a uterine manipulator.

14. The medical instrument of claim 10, further comprising:
  an elongate hollow body comprising surgical grade material, the elongate hollow body extending in a longitudinal direction from a proximal end to a distal end;
  wherein the probe is disposed at the distal end of the elongate hollow body.

15. A method of using a medical instrument to perform a laparoscopic oncology procedure, the method comprising:
  inserting a probe of the medical instrument into the human vaginal cavity, the probe comprising:
  an outer circumferential surface, the outer circumferential surface extending in a longitudinal direction and sized for non-traumatic insertion into a human vaginal cavity, wherein the outer circumferential surface is substantially cylindrical; and
  a lip projecting outwardly from the outer circumferential surface and extending circumferentially about only a portion of the outer circumferential surface, the lip configured to raise vaginal tissue to provide a visual landmark for dissection during the laparoscopic oncology procedure, the lip positioned such that the lip is set back from a distal-most point of the probe by approximately 20 millimeters and the outer circumferential surface extends both distally and proximally to the lip,
  wherein the outer circumferential surface comprises a surgical grade material comprising sufficient stiffness to support the lip in raising the vaginal tissue to provide the visual landmark for dissection during the laparoscopic oncology procedure, and
  wherein the probe comprises a hollow inner cavity;
  positioning the lip of the medical instrument to act as a visual landmark that indicates where a surgeon should cut to remove a cuff from the vagina to excise cancer tissue;
  cutting vaginal tissue to remove the cuff; and
  removing the probe from the vaginal cavity.

16. The medical instrument of claim 15, wherein the lip extends circumferentially about the outer circumferential surface through an arc that subtends an angle of at least 100 degrees.

17. The medical instrument of claim 15, wherein the probe further comprises:
  a passage configured to enable a medical device to pass therethrough; and
  the medical device, wherein the medical device comprises a uterine manipulator.

18. The medical instrument of claim 15, further comprising:
  an elongate hollow body comprising surgical grade material, the elongate hollow body extending in a longitudinal direction from a proximal end to a distal end;
  wherein the probe is disposed at the distal end of the elongate hollow body.

19. The medical instrument of claim 15, further comprising:
  a second lip projecting outwardly from the outer circumferential surface and extending circumferentially about only a portion of the outer circumferential surface, the second lip configured to raise vaginal tissue to provide a visual landmark for dissection, the second lip positioned such that at least a portion of the second lip extends distally beyond a distal end of the outer circumferential surface.

20. A medical instrument for performing a laparoscopic oncology procedure, the medical instrument comprising:
  a probe comprising:
  an outer circumferential surface, the outer circumferential surface extending in a longitudinal direction and sized for non-traumatic insertion into a human vaginal cavity, wherein the outer circumferential surface is substantially cylindrical; and
  a lip projecting outwardly from the outer circumferential surface and extending circumferentially about only a portion of the outer circumferential surface, the lip configured to raise vaginal tissue to provide a visual landmark for dissection during the laparoscopic oncology procedure, the lip positioned such that the lip is set back from a distal-most point of the probe by approximately 20 millimeters and the outer circumferential surface extends both distally and proximally to the lip,
  wherein the outer circumferential surface comprises a surgical grade material comprising sufficient stiffness to support the lip in raising the vaginal tissue to provide the visual landmark for dissection during the laparoscopic oncology procedure,
  wherein the probe comprises a hollow inner cavity, and
  wherein the lip further comprises:
  a distal face angled proximally with respect to a longitudinal axis of the instrument; and
  a proximal face angled distally with respect to the longitudinal axis of the instrument; and
  a second lip projecting outwardly from the outer circumferential surface and extending circumferentially about only a portion of the outer circumferential surface, the second lip configured to raise vaginal tissue to provide a visual landmark for dissection, the second lip positioned such that at least a portion of the second lip extends distally beyond a distal end of the outer circumferential surface.

21. The medical instrument of claim 20, wherein the lip extends circumferentially about the outer circumferential surface through an arc that subtends an angle of at least 100 degrees.

22. The medical instrument of claim 20, wherein the probe further comprises:
  a passage configured to enable a medical device to pass therethrough; and
  the medical device, wherein the medical device comprises a uterine manipulator.

23. The medical instrument of claim 20, further comprising:
  an elongate hollow body comprising surgical grade material, the elongate hollow body extending in a longitudinal direction from a proximal end to a distal end;

wherein the probe is disposed at the distal end of the elongate hollow body.

24. The medical instrument of claim 20, wherein the second lip comprises the distal-most point of the probe.

25. A medical instrument for performing a laparoscopic oncology procedure, the medical instrument comprising:
a probe comprising:
an outer circumferential surface, the outer circumferential surface extending in a longitudinal direction and sized for non-traumatic insertion into a human vaginal cavity, wherein the outer circumferential surface is substantially cylindrical; and
a lip projecting outwardly from the outer circumferential surface and extending circumferentially about only a portion of the outer circumferential surface, the lip configured to raise vaginal tissue to provide a visual landmark for dissection during the laparoscopic oncology procedure, the lip positioned such that the lip is set back from a distal-most point of the probe by approximately 20 millimeters and the outer circumferential surface extends both distally and proximally to the lip;
wherein the outer circumferential surface comprises a surgical grade material comprising sufficient stiffness to support the lip in raising the vaginal tissue to provide the visual landmark for dissection during the laparoscopic oncology procedure,
wherein the probe comprises a hollow inner cavity, and
wherein the circumferential surface extends proximally from the lip toward a tapered region that is tapered radially inwardly in a proximal direction; and
a second lip projecting outwardly from the outer circumferential surface and extending circumferentially about only a portion of the outer circumferential surface, the second lip configured to raise vaginal tissue to provide a visual landmark for dissection, the second lip positioned such that at least a portion of the second lip extends distally beyond a distal end of the outer circumferential surface.

26. The medical instrument of claim 25, wherein the lip extends circumferentially about the outer circumferential surface through an arc that subtends an angle of at least 100 degrees.

27. The medical instrument of claim 25, wherein sides of the lip transition smoothly from the outer circumferential surface to limit damage to body tissue when the medical instrument is rotated within the human vaginal cavity.

28. The medical instrument of claim 25, wherein the lip comprises a tapered shape that is wider adjacent the outer circumferential surface than at an outer edge of the lip.

29. The medical instrument of claim 25, wherein the outer circumferential surface comprises a diameter of approximately 40 millimeters.

30. The medical instrument of claim 25, wherein the probe further comprises:
a passage configured to enable a medical device to pass therethrough; and
the medical device, wherein the medical device comprises a uterine manipulator.

31. The medical instrument of claim 25, wherein the probe is tapered at the distal-most point of the probe, wherein a first diameter of the distal-most point of the probe is larger than a second diameter of a proximal end of the probe.

32. The medical instrument of claim 25, further comprising:
an elongate hollow body comprising surgical grade material, the elongate hollow body extending in a longitudinal direction from a proximal end to a distal end;
wherein the probe is disposed at the distal end of the elongate hollow body.

33. The medical instrument of claim 25, wherein the second lip comprises the distal-most point of the probe.

34. A medical instrument for performing a laparoscopic oncology procedure, the medical instrument comprising:
a probe comprising:
an outer circumferential surface, the outer circumferential surface extending in a longitudinal direction and sized for non-traumatic insertion into a human vaginal cavity; and
a lip projecting outwardly from the outer circumferential surface and extending circumferentially about only a portion of the outer circumferential surface, the lip configured to raise vaginal tissue to provide a visual landmark for dissection during the laparoscopic oncology procedure, the lip positioned such that the lip is set back from a distal-most point of the probe and the outer circumferential surface extends both distally and proximally to the lip,
wherein the outer circumferential surface comprises a surgical grade material comprising sufficient stiffness to support the lip in raising the vaginal tissue to provide the visual landmark for dissection during the laparoscopic oncology procedure,
wherein the lip comprises a tapered shape that is wider adjacent the outer circumferential surface than at an outer edge of the lip, and
wherein the lip further comprises:
a distal face angled proximally with respect to a longitudinal axis of the instrument; and
a proximal face angled distally with respect to the longitudinal axis of the instrument; and
a second lip projecting outwardly from the outer circumferential surface and extending circumferentially about only a portion of the outer circumferential surface, the second lip configured to raise vaginal tissue to provide a visual landmark for dissection, the second lip positioned such that at least a portion of the second lip extends distally beyond a distal end of the outer circumferential surface.

35. The medical instrument of claim 34, wherein the probe further comprises:
a passage configured to enable a medical device to pass therethrough; and
the medical device, wherein the medical device comprises a uterine manipulator.

36. The medical instrument of claim 34, wherein
the second lip comprises the distal-most point of the probe.

37. A medical instrument for performing a laparoscopic oncology procedure, the medical instrument comprising:
a probe comprising:
an outer circumferential surface, the outer circumferential surface extending in a longitudinal direction and sized for non-traumatic insertion into a human vaginal cavity; and
a lip projecting outwardly from the outer circumferential surface and extending circumferentially about only a portion of the outer circumferential surface, the lip configured to raise vaginal tissue to provide a visual landmark for dissection during the laparoscopic oncology procedure, the lip positioned such that the lip is set back from a distal-most point of the probe and the outer circumferential surface extends both distally and proximally to the lip, wherein the outer circumferential surface comprises a surgical grade material comprising sufficient stiffness to support the lip in raising the vaginal tissue to provide the visual landmark for dissection during the laparoscopic oncology procedure, wherein the lip comprises a tapered shape that is wider adjacent the outer circumferential surface than at an outer edge of the lip, and wherein the circumferential surface extends proximally from the lip toward a tapered region that is tapered radially inwardly in a proximal direction; and a pneumatic plug configured to pneumatically plug at least a portion of the probe.

38. The medical instrument of claim 37, wherein a second lip comprises the distal-most point of the probe.

39. The medical instrument of claim 37, further comprising:

an elongate hollow body comprising surgical grade material, the elongate hollow body extending in a longitudinal direction from a proximal end to a distal end;

wherein the probe is disposed at the distal end of the elongate hollow body; and a second probe disposed at the proximal end of the elongate body, the second probe comprising a second outer circumferential surface comprising a different diameter than the outer circumferential surface of the probe disposed at the distal end of the elongate body.

40. The medical instrument of claim 37, wherein the probe comprises a hollow inner cavity.

41. The medical instrument of claim 37, wherein the outer circumferential surface is substantially cylindrical.

42. The medical instrument of claim 37, wherein the probe further comprises:

a passage configured to enable a medical device to pass therethrough; and the medical device, wherein the medical device comprises a uterine manipulator.

43. A medical instrument for performing a laparoscopic oncology procedure, the medical instrument comprising:

a probe comprising:

an outer circumferential surface, the outer circumferential surface extending in a longitudinal direction and sized for non-traumatic insertion into a human vaginal cavity; and a lip projecting outwardly from the outer circumferential surface and extending circumferentially about only a portion of the outer circumferential surface, the lip configured to raise vaginal tissue to provide a visual landmark for dissection during the laparoscopic oncology procedure, the lip positioned such that the lip is set back from a distal-most point of the probe and the outer circumferential surface extends both distally and proximally to the lip, wherein the outer circumferential surface comprises a surgical grade material comprising sufficient stiffness to support the lip in raising the vaginal tissue to provide the visual landmark for dissection during the laparoscopic oncology procedure, wherein the lip comprises a tapered shape that is wider adjacent the outer circumferential surface than at an outer edge of the lip; and a second lip projecting outwardly from the outer circumferential surface and extending circumferentially about only a portion of the outer circumferential surface, the second lip configured to raise vaginal tissue to provide a visual landmark for dissection, the second lip positioned such that at least a portion of the second lip extends distally beyond a distal end of the outer circumferential surface.

44. The medical instrument of claim 43, wherein the probe further comprises:

a passage configured to enable a medical device to pass therethrough; and the medical device, wherein the medical device comprises a uterine manipulator.

45. The medical instrument of claim 43, wherein the second lip comprises the distal-most point of the probe.

* * * * *